United States Patent [19]
Arakawa et al.

[11] Patent Number: 5,998,170
[45] Date of Patent: Dec. 7, 1999

[54] POLYNUCLEOTIDES ENCODING HEPATOCYTE-SPECIFIC MEMBERS OF THE FGF FAMILY

[75] Inventors: Tsutomu Arakawa, Thousand Oaks; Dimitry Michael Danilenko, Camarillo, both of Calif.; Nobuyuki Itoh, Ohtsu, Japan; Francis Hall Martin, Newbury Park, Calif.

[73] Assignee: Amgen Inc., Thousand Oaks, Calif.

[21] Appl. No.: 08/943,915

[22] Filed: Oct. 3, 1997

[51] Int. Cl.[6] .......................... C07K 14/50; C12N 15/18; C12N 15/63

[52] U.S. Cl. .................. 435/69.4; 435/71.1; 435/243; 435/252.33; 435/320.1; 435/325; 530/399; 536/23.51

[58] Field of Search ................... 435/69.4, 325, 435/243, 320.1; 536/23.51; 530/399

[56] References Cited

PUBLICATIONS

George et al. Macromolecular Seq. & Sym. Selected Methods & Applications, pp. 127–149, 1988.
Lokker et al. EMBO J. 11(7): 2503–2510, 1992.
Baird et al., Cancer Cells, vol. 3, pp. 239–243 (1991).
Burgess and Maciag, Annu. Rev. Biochem., vol. 58, pp. 575–606 (1989).
Dickson et al., Annals of the New York Academy of Sciences, vol. 683, pp. 18–26 (1991).
Yoshida et al., Annals of the New York Academy of Sciences, vol. 683, pp. 27–37 (1991).
Goldfarb et al., Annals of the New York Academy of Sciences, vol. 683, pp. 38–52 (1991).
Coulier et al., Annals of the New York Academy of Sciences, vol. 683, pp. 53–61 (1991).
Aaronson et al., Annals of the New York Academy of Sciences, vol. 683, pp. 62–77 (1991).
Tanaka et al, Proc. Natl. Acad. Sci. USA, vol. 89, pp. 8928–8932 (1991).
Miyamoto et al., Molecular and Cellular Biology, vol. 13, No. 7, pp. 4251–4259 (1993).
Yamasaki et al., Journal of Biological Chemistry, vol. 271, No. 27, pp. 15918–15921 (1996).
Smallwood et al., Proc. Natl. Acad. Sci. USA, vol. 93, pp. 9850–9857 (1996).
Coulier et al., Journal of Molecular Evolution, vol. 44, pp. 43–56 (1997).

*Primary Examiner*—Lila Feisee
*Assistant Examiner*—Christine Saoud
*Attorney, Agent, or Firm*—Richard J. Mazza; Ron K. Levy; Steven M. Odre

[57] ABSTRACT

Nucleic acid molecules are described which are useful in vectors, transformed or transfected host cells, and methods for the recombinant expression of hepatocyte growth-specific polypeptide members of the FGF family.

19 Claims, 9 Drawing Sheets

FIG. 1A

```
CGCCGCCGGCCCGCC ATG GCG GAG GTC GGG GGC GTC TTT GCC TCC TTG                    49
                Met Ala Glu Val Gly Gly Val Phe Ala Ser Leu
                 1                   5                  10

GAC TGG GAC CTG CAA GGC TTC TCC TCT CTG GGG AAC GTG CCC TTA                    97
Asp Trp Asp Leu Gln Gly Phe Ser Ser Leu Gly Asn Val Pro Leu
             15                  20                  25

GCT GAC TCC CCG GGT TTC CTG AAC GAG CGC CTG GGC ATC GAG GGG                   145
Ala Asp Ser Pro Gly Phe Leu Asn Glu Arg Leu Gly Ile Glu Gly
         30                  35                  40

AAG CTG CAG CGC CGC TCG CCC CAG CTC GCC CAC CTG AAG GGG ATC                   193
Lys Leu Gln Arg Arg Ser Pro Gln Leu Ala His Leu Lys Gly Ile
     45                  50                  55

CTG CGG CGC CAG CTC TAC TGC ACA GAC TTC GCC TTC CAC CTT GAA ATC               241
Leu Arg Arg Gln Leu Tyr Cys Thr Asp Phe Ala Phe His Leu Glu Ile
 60                  65                  70                  75

TTC CCC AAT GGC ACG GTG CAT GGC ACC CGC TAC CAC GAC CAC AGC TTC               289
Phe Pro Asn Gly Thr Val His Gly Thr Arg Tyr His Asp His Ser Arg Phe
             80                  85                                90

GGA ATT CTG GAA TTT ATC AGC TTG GCT GTG GGG CTG ATC AGC ATC CGG               337
Gly Ile Leu Glu Phe Ile Ser Leu Ala Val Gly Leu Ile Ser Ile Arg
         95                 100                 105

GGA GTA GAC TCT GGC CTA TAC CTA GGA ATG AAT GAG CGA GGA GAG CTG               385
Gly Val Asp Ser Gly Leu Tyr Leu Gly Met Asn Glu Arg Gly Glu Leu
    110                 115                 120
```

FIG. 1B

```
TTT GGA TCG AAG AAA CTC ACA CGA GAA TGT GTT TTC CGG GAA CAG TTT    433
Phe Gly Ser Lys Lys Leu Thr Arg Glu Cys Val Phe Arg Glu Gln Phe
125                             130                         135

GAA GAA AAC TGG TAC AAC ACC TAT GCA TCC ACC TTG TAC AAA CAC TCG    481
Glu Glu Asn Trp Tyr Asn Thr Tyr Ala Ser Thr Leu Tyr Lys His Ser
140                 145                         150             155

GAC TCG GAG AGA CAG TAT GTG GCC CTG AAT AAA GAC GGC TCA CCC        529
Asp Ser Glu Arg Gln Tyr Val Ala Leu Asn Lys Asp Gly Ser Pro
            160                         165                 170

CGG GAG GGA TAC AGG ACT AAA CGA CAC CAG AAA TTC ACT CAC TTT TTA    577
Arg Glu Gly Tyr Arg Thr Lys Arg His Gln Lys Phe Thr His Phe Leu
        175                         180                     185

CCC AGG CCA GTA GAT CCT TCT AAG TTG CCC TCC ATG TCC AGA GAC CTC    625
Pro Arg Pro Val Asp Pro Ser Lys Leu Pro Ser Met Ser Arg Asp Leu
190                         195                         200

TTC CGC TAT AGG TAA TGGACCCCTGGTGCCA                               656
Phe Arg Tyr Arg
205
```

FIG.2

```
FGF-16  MA---EVGGVFASLDWDLQGFSSSLGNVP-LA-DSPGFLNERLGQIE-GKLQRGSP-TDFAH    55
         **  ***  *     ****  ***  * *   * * *   *   *
FGF-9   MAPLGEVGSYFGVQDAVPF-----GNVPVLPVDSPVLLSDHLGQSEAGGLPRGPAVTDLDH    56

LKGILRRRQLYCRTGFHLEIFPNGTVSGTRKDHSRFGILEFISLAVGLISIRGVDSGLYL    115
        ***********  **********    ************* ***** **********
        LKGILRRRQLYCRTGFHLEIFPNGTIQGTRKDHSRFGILEFISIAVGLVSIRGVDSGLYL    115

GMNERGELFGSKKLTRECVFREQFEENWYNTYASTLYKHSDSERQYYVALNKDGSPREGY    175
        **** ** ** *******  *** ******************   **************
        GMNEKGELYGSEKLTQECVFREQFEENWYNTYSSNLYKHVDTGRRYYVALNKDGTPREGT    176

RTKRHQKFTHFLPRPVDPSKLPSMSRDLFRYR    207
        ******************** *
        RTKRHQKFTHFLPRPVDPDKVPELYKDILSQS    208
```

FIG. 6A

```
CAGCGCCGCAATCGGCCCAGCC                                                              52

ATG GCA GAG GTG GGG GGC GTC TTC GCC TCC                                             100
Met Ala Glu Val Gly Gly Val Phe Ala Ser
 1                    5                 10

TTG GAC TGG GAT CTA CAC GGC TTC TCC TCG TCT CTG GGG AAC GTG CCC                     148
Leu Asp Trp Asp Leu His Gly Phe Ser Ser Ser Leu Gly Asn Val Pro
              15                      20                      25

TTA GCT GAC TCC CCA GGT TTC CTG AAC GAG CGC CTG GGC CAA ATC GAG                     196
Leu Ala Asp Ser Pro Gly Phe Leu Asn Glu Arg Leu Gly Gln Ile Glu
              30                      35                      40

GGG AAG CTG CAG CGT GGC TCA CCC ACA GAC TTC GCC CAC CTG AAG GGG                     244
Gly Lys Leu Gln Arg Gly Ser Pro Thr Asp Phe Ala His Leu Lys Gly
              45                      50                      55

ATC CTG CGG CGC CAG CTC TAC TGC CGC ACC GGC TTC CAC CTG GAG                         292
Ile Leu Arg Arg Gln Leu Tyr Cys Arg Thr Gly Phe His Leu Glu
              60                      65              70

ATC TTC CCC AAC GGC ACG GTG CAC GGG ACC CGC CAC GAC CAC AGC CGC                     340
Ile Phe Pro Asn Gly Thr Val His Gly Thr Arg His Asp His Ser Arg
              75                      80                      85              90

TTC GGA ATC CTG GAG TTT ATC AGC CTG GCT GTG GGG CTG ATC AGC ATC                     388
Phe Gly Ile Leu Glu Phe Ile Ser Leu Ala Val Gly Leu Ile Ser Ile
              95                     100                     105

CGG GGA GTG GAC TCT GGC CTG TAC CTA GGA ATG AAT GAG CGA GGA GAA
Arg Gly Val Asp Ser Gly Leu Tyr Leu Gly Met Asn Glu Arg Gly Glu
             110                     115                     120
```

FIG. 6B

```
CTC TAT GGG TCG AAG AAA CTC ACA CGT GAA TGT GTT TTC CGG GAA CAG    436
Leu Tyr Gly Ser Lys Lys Leu Thr Arg Glu Cys Val Phe Arg Glu Gln
125                         130                 135

TTT GAA AAC TGG TAC AAC ACC TAT GCC TCA ACC TTG TAC AAA CAT       484
Phe Glu Asn Trp Tyr Asn Thr Tyr Ala Ser Thr Leu Tyr Lys His
140                         145                 150

TCG GAC TCA GAG AGA CAG TAT TAC GTG GCC CTG AAC AAA GAT GGC TCA   532
Ser Asp Ser Glu Arg Gln Tyr Tyr Val Ala Leu Asn Lys Asp Gly Ser
155                         160                 165                 170

CCC CGG GAG GGA TAC AGG ACT AAA CGA CAC CAG AAA TTC ACT CAC TTT   580
Pro Arg Glu Gly Tyr Arg Thr Lys Arg His Gln Lys Phe Thr His Phe
175                         180                 185

TTA CCC AGG CCT GTA GAT CCT TCT AAG TTG CCC TCC ATG TCC AGA GAC   628
Leu Pro Arg Pro Val Asp Pro Ser Lys Leu Pro Ser Met Ser Arg Asp
190                         195                 200

CTC TTT CAC TAT AGG TAA TGAACCTCTGGTGTGCCCTCTGTGACCC              674
Leu Phe His Tyr Arg
205
```

FIG.7A
FIG.7B
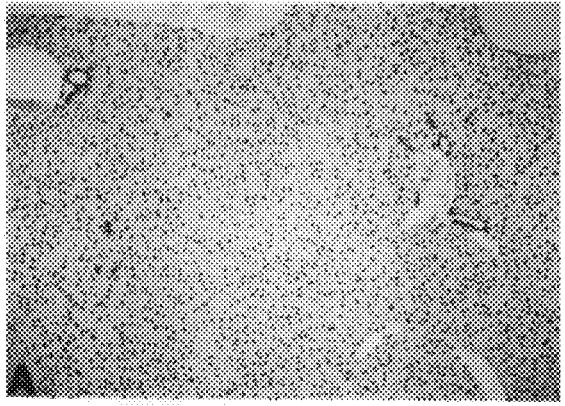
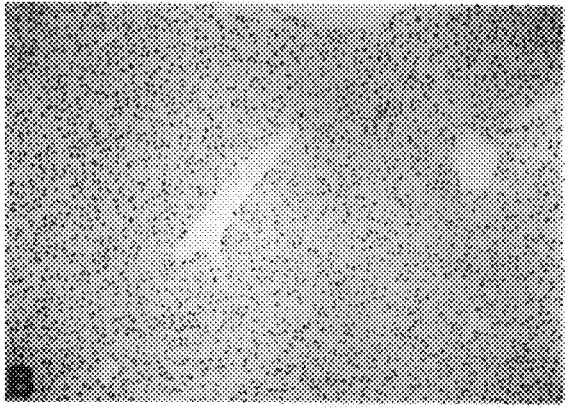
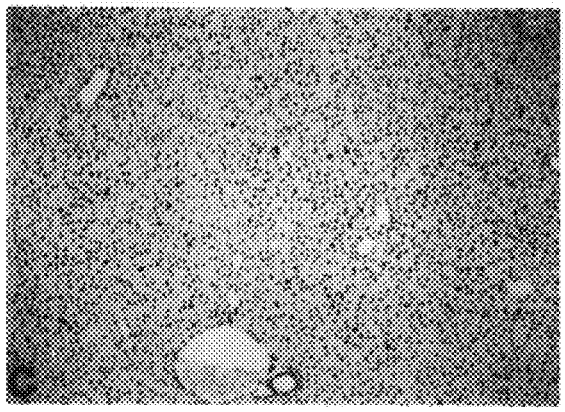
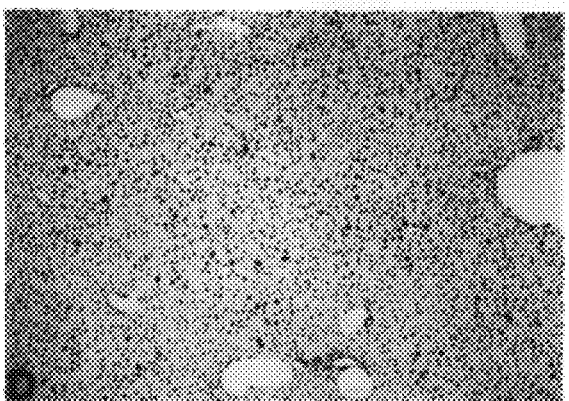
FIG.7C
FIG.7D

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATGGCGGAGG TCGGGGGCGT CTTTGCCTCC TTGGACTGGG ACCTGCAAGG CTTCTCCTCC      60

TCTCTGGGGA ACGTGCCCTT AGCTGACTCC CCGGGTTTCC TGAACGAGCG CCTGGGCCAG     120

ATCGAGGGGA AGCTGCAGCG CGGCTCGCCC ACAGACTTCG CCCACCTGAA GGGGATCCTG     180

CGGCGCCGCC AGCTCTACTG CCGCACGGGC TTCCACCTTG AAATCTTCCC CAATGGCACG     240

GTGCATGGCA CCCGCCACGA CCACAGCCGC TTCGGAATTC TGGAATTTAT CAGCTTGGCT     300

GTGGGGCTGA TCAGCATCCG GGGAGTAGAC TCTGGCCTAT ACCTAGGAAT GAATGAGCGA     360

GGAGAGCTGT TTGGATCGAA GAAACTCACA CGAGAATGTG TTTTCCGGGA ACAGTTTGAA     420

GAAAACTGGT ACAACACCTA TGCATCCACC TTGTACAAAC ACTCGGACTC GGAGAGACAG     480

TATTATGTGG CCCTGAATAA AGACGGCTCA CCCCGGGAGG GATACAGGAC TAAACGACAC     540

CAGAAATTCA CTCACTTTTT ACCCAGGCCA GTAGATCCTT CTAAGTTGCC CTCCATGTCC     600

AGAGACCTCT TCCGCTATAG G                                               621
```

(2) INFORMATION FOR SEQ ID NO:2:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Glu Val Gly Gly Val Phe Ala Ser Leu Asp Trp Asp Leu Gln
1               5                   10                  15

Gly Phe Ser Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
            35                  40                  45

Ser Pro Thr Asp Phe Ala His Leu Lys Gly Ile Leu Arg Arg Arg Gln
        50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Phe Gly Ser Lys Lys
        115                 120                 125

Leu Thr Arg Glu Cys Val Phe Arg Glu Gln Phe Glu Glu Asn Trp Tyr
```

```
                130                 135                 140
Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
                180                 185                 190

Pro Ser Lys Leu Pro Ser Met Ser Arg Asp Leu Phe Arg Tyr Arg
                195                 200                 205
```

(2) INFORMATION FOR SEQ ID NO:3:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ala Pro Leu Gly Glu Val Gly Ser Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
                35                  40                  45

Pro Ala Val Thr Asp Leu Asp His Leu Lys Gly Ile Leu Arg Arg Arg
50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205
```

(2) INFORMATION FOR SEQ ID NO:4:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

ATGGCAGAGG TGGGGGGCGT CTTCGCCTCC TTGGACTGGG ATCTACACGG CTTCTCCTCG    60

```
TCTCTGGGGA ACGTGCCCTT AGCTGACTCC CCAGGTTTCC TGAACGAGCG CCTGGGCCAA    120

ATCGAGGGGA AGCTGCAGCG TGGCTCACCC ACAGACTTCG CCCACCTGAA GGGGATCCTG    180

CGGCGCCGCC AGCTCTACTG CCGCACCGGC TTCCACCTGG AGATCTTCCC CAACGGCACG    240

GTGCACGGGA CCCGCCACGA CCACAGCCGC TTCGGAATCC TGGAGTTTAT CAGCCTGGCT    300

GTGGGGCTGA TCAGCATCCG GGGAGTGGAC TCTGGCCTGT ACCTAGGAAT GAATGAGCGA    360

GGAGAACTCT ATGGGTCGAA GAAACTCACA CGTGAATGTG TTTTCCGGGA ACAGTTTGAA    420

GAAAACTGGT ACAACACCTA TGCCTCAACC TTGTACAAAC ATTCGGACTC AGAGAGACAG    480

TATTACGTGG CCCTGAACAA AGATGGCTCA CCCCGGGAGG GATACAGGAC TAAACGACAC    540

CAGAAATTCA CTCACTTTTT ACCCAGGCCT GTAGATCCTT CTAAGTTGCC CTCCATGTCC    600

AGAGACCTCT TTCACTATAG G                                              621
```

(2) INFORMATION FOR SEQ ID NO:5:

(i) SEQUENCE CHARACTERISTICS:
  (A) LENGTH: 207 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:5:

```
Met Ala Glu Val Gly Gly Val Phe Ala Ser Leu Asp Trp Asp Leu His
  1               5                  10                  15

Gly Phe Ser Ser Leu Gly Asn Val Pro Leu Ala Asp Ser Pro Gly
                 20                  25                  30

Phe Leu Asn Glu Arg Leu Gly Gln Ile Glu Gly Lys Leu Gln Arg Gly
                 35                  40                  45

Ser Pro Thr Asp Phe Ala His Leu Lys Gly Ile Leu Arg Arg Arg Gln
 50                  55                  60

Leu Tyr Cys Arg Thr Gly Phe His Leu Glu Ile Phe Pro Asn Gly Thr
 65                  70                  75                  80

Val His Gly Thr Arg His Asp His Ser Arg Phe Gly Ile Leu Glu Phe
                 85                  90                  95

Ile Ser Leu Ala Val Gly Leu Ile Ser Ile Arg Gly Val Asp Ser Gly
                100                 105                 110

Leu Tyr Leu Gly Met Asn Glu Arg Gly Glu Leu Tyr Gly Ser Lys Lys
                115                 120                 125

Leu Thr Arg Glu Cys Val Phe Arg Glu Gln Phe Glu Glu Asn Trp Tyr
130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
                180                 185                 190

Pro Ser Lys Leu Pro Ser Met Ser Arg Asp Leu Phe His Tyr Arg
                195                 200                 205
```

(2) INFORMATION FOR SEQ ID NO:6:

(i) SEQUENCE CHARACTERISTICS:
  (A) LENGTH: 13 amino acids
  (B) TYPE: amino acid
  (C) STRANDEDNESS: single (D) TOPOLOGY: linear (ii) MOLECULE TYPE: peptide (xi) SEQUENCE DESCRIPTION: SEQ ID NO:6:

Gly Ala Pro Val Pro Tyr Pro Asp Pro Leu Glu Pro Arg
1               5                   10

(2) INFORMATION FOR SEQ ID NO:7:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:7:

CCCTTAGCTG ACTCCCCGGG TTTCCTGAAC GAGCGCCTGG GCCAGATCGA GGGGAAGCTG      60

CAGCGCGGCT CGCCCACAGA CTTCGCCCAC CTGAAGGGGA TCCTGCGGCG CCGCCAGCTC     120

TACTGCCGCA CGGGCTTCCA CCTTGAAATC TTCCCCAATG GCACGGTGCA TGGCACCCGC     180

CACGACCACA GCCGCTTCGG AATTCTGGAA TTTATCAGCT TGGCTGTGGG GCTGATCAGC     240

ATCCGGGGAG TAGACTCTGG CCTATACCTA GGAATGAATG AGCGAGGAGA GCTGTTTGGA     300

TCGAAGAAAC TCACACGAGA ATGTGTTTTC CGGGAACAGT TTGAAGAAAA CTGGTACAAC     360

ACCTATGCAT CCACCTTGTA CAAACACTCG GACTCGGAGA GACAGTATTA TGTGGCCCTG     420

AATAAAGACG GCTCACCCCG GGAGGGATAC AGGACTAAAC GACACCAGAA ATTCACTCAC     480

TTTTTACCCA GGCCAGTAGA TCCTTCTAAG TTGCCCTCCA TGTCCAGAGA CCTCTT         536

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:8:

CGGGAACAGT TTGAAGAAAA CTGGTA                                           26

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION: 8
        (D) OTHER INFORMATION: /note= "The "N" denotes Inosine"

(xi) SEQUENCE DESCRIPTION: SEQ ID NO:9:

GAAAGTGNGT GAACTTTCTG AGTG                                             24

(2) INFORMATION FOR SEQ ID NO:10:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "OLIGONUCLEOTIDE"

(xi) SEQUENCE DESCRIPTION: SEQ ID NO:10:

CCGCACGGGC TTCCACCTTG A                                          21

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION: 18..23
        (D) OTHER INFORMATION: /note= "The "N" at positions 18-23
            denotes random base (A, C, T, or G)"

(xi) SEQUENCE DESCRIPTION: SEQ ID NO:11:

GGCCGGATAG GCCTCACNNN NNNT                                       24

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:12:

CGCGGCTCGC CCACAGACTT C                                          21

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:13:

CTGTCTCTCT GAGTCCGAAT GTT                                        23

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:14:

TTCGGCCGGA TAGGCCTTTT TTTTTTTTTT                                        30

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:15:

GTACAACACC TATGCCTCAA CCT                                               23

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:16:

GCAGTCGCTC CTTCCGTG                                                     18

(2) INFORMATION FOR SEQ ID NO:17:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(ix) FEATURE:
        (A) NAME/KEY: misc_feature
        (B) LOCATION: 1..9
        (D) OTHER INFORMATION: /note= ""N" denotes random base"

(xi) SEQUENCE DESCRIPTION: SEQ ID NO:17:

NNNNNNNNN                                                               9

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION: 18..28
        (D) OTHER INFORMATION: /note= "The "N" at positions 18-28
            denotes random base (A, C, T, or G)"

(xi) SEQUENCE DESCRIPTION: SEQ ID NO:18:

GCAGTCGCTC CTTCCGTGNN NNNNNNN                                           28

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:19:

CTCCTCGCTC ATTCATTCCT A                                                  21

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:20:

AGTCCACTCC CCGGATGCTG AT                                             22

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:21:

CTCCAGGATT CCGAAGCGGC TGTGGTCGTG                                  30

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(ix) FEATURE:
        (A) NAME/KEY: misc_feature
        (B) LOCATION: one-of(1, 2, 5, 6, 9, 14, 18, 19, 20, 21, 22)
        (D) OTHER INFORMATION: /note= "The "N" at positions 1, 2,
            5, 6, 9, 14, and 18 denote "Inosine" and at positions
            19-22 random bases"

(xi) SEQUENCE DESCRIPTION: SEQ ID NO:22:

NNTANNACNC CACNCAANNN NNATG                                          25

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "OLIGONUCLEOTIDE"

(xi) SEQUENCE DESCRIPTION: SEQ ID NO:23:

GGTAGGACGC CACGCAAG                                          18

(2) INFORMATION FOR SEQ ID NO:24:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OLIGONUCLEOTIDE"

(xi) SEQUENCE DESCRIPTION: SEQ ID NO:24:

TCCGAAGCGG CTGTGGTCGT G                                      21

(2) INFORMATION FOR SEQ ID NO:25:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OLIGONUCLEOTIDE"

(xi) SEQUENCE DESCRIPTION: SEQ ID NO:25:

GGATCTACAC GGCTTCTCCT CGTCT                                  25

(2) INFORMATION FOR SEQ ID NO:26:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OLIGONUCLEOTIDE"

(xi) SEQUENCE DESCRIPTION: SEQ ID NO:26:

CTGGGGAGTC AGCTAAGGGC A                                      21

(2) INFORMATION FOR SEQ ID NO:27:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "OLIGONUCLEOTIDE"

(xi) SEQUENCE DESCRIPTION: SEQ ID NO:27:

AAACAACATA TGGCTGAAGT TGGTGGTGTC TTTGCCTCCT TGGA              44

(2) INFORMATION FOR SEQ ID NO:28:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: other nucleic acid (A) DESCRIPTION: /desc = "OLIGONUCLEOTIDE"

(xi) SEQUENCE DESCRIPTION: SEQ ID NO:28:

AAACAAGGTA CCTTTACCTA TAGCGGAAGA GGT                33

(2) INFORMATION FOR SEQ ID NO:29:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "OLIGONUCLEOTIDE"

(xi) SEQUENCE DESCRIPTION: SEQ ID NO:29:

CGTACAGGTT TACGCAAGAA AATGG                         25

(2) INFORMATION FOR SEQ ID NO:30:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "OLIGONUCLEOTIDE"

(xi) SEQUENCE DESCRIPTION: SEQ ID NO:30:

TATGAACGAG CGCCTGGGCC AGATCGAGGG GAAGCTGCA          39

(2) INFORMATION FOR SEQ ID NO:31:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "OLIGONUCLEOTIDE"

(xi) SEQUENCE DESCRIPTION: SEQ ID NO:31:

GCTTCCCCTC GATCTGGCCC AGGCGCTCGT TCA                33

(2) INFORMATION FOR SEQ ID NO:32:

(i) SEQUENCE CHARACTERISTICS:
      (A) LENGTH: 173 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:32:

Asn Glu Arg Leu Gly Gln Ile Glu Gly Lys Leu Gln Arg Gly Ser Pro
1               5                   10                  15

Thr Asp Phe Ala His Leu Lys Gly Ile Leu Arg Arg Gln Leu Tyr
            20                  25                  30

Cys Arg Thr Gly Phe His Leu Glu Ile Phe Pro Asn Gly Thr Val His
            35                  40                  45

Gly Thr Arg His Asp His Ser Arg Phe Gly Ile Leu Glu Phe Ile Ser
            50                  55                  60

Leu Ala Val Gly Leu Ile Ser Ile Arg Gly Val Asp Ser Gly Leu Tyr

```
                    65                  70                  75                  80
Leu Gly Met Asn Glu Arg Gly Glu Leu Phe Gly Ser Lys Lys Leu Thr
                    85                  90                  95
Arg Glu Cys Val Phe Arg Glu Gln Phe Glu Glu Asn Trp Tyr Asn Thr
                100                 105                 110
Tyr Ala Ser Thr Leu Tyr Lys His Ser Asp Ser Glu Arg Gln Tyr Tyr
                115                 120                 125
Val Ala Leu Asn Lys Asp Gly Ser Pro Arg Glu Gly Tyr Arg Thr Lys
                130                 135                 140
Arg His Gln Lys Phe Thr His Phe Leu Pro Arg Pro Val Asp Pro Ser
145                 150                 155                 160
Lys Leu Pro Ser Met Ser Arg Asp Leu Phe Arg Tyr Arg
                    165                 170

(2) INFORMATION FOR SEQ ID NO:33:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Ser Leu Asp Trp Asp Leu Gln Gly Phe Ser Ser Leu Gly Asn Val
1                   5                  10                  15

Pro Leu Ala Asp Ser Pro Gly Phe Leu Asn Glu Arg Leu Gly Gln Ile
                    20                  25                  30

Glu Gly Lys Leu Gln Arg Gly Ser Pro Thr Asp Phe Ala His Leu Lys
                35                  40                  45

Gly Ile Leu Arg Arg Arg Gln Leu Tyr Cys Arg Thr Gly Phe His Leu
                50                  55                  60

Glu Ile Phe Pro Asn Gly Thr Val His Gly Thr Arg His Asp His Ser
65                  70                  75                  80

Arg Phe Gly Ile Leu Glu Phe Ile Ser Leu Ala Val Gly Leu Ile Ser
                    85                  90                  95

Ile Arg Gly Val Asp Ser Gly Leu Tyr Leu Gly Met Asn Glu Arg Gly
                100                 105                 110

Glu Leu Phe Gly Ser Lys Lys Leu Thr Arg Glu Cys Val Phe Arg Glu
                115                 120                 125

Gln Phe Glu Glu Asn Trp Tyr Asn Thr Tyr Ala Ser Thr Leu Tyr Lys
                130                 135                 140

His Ser Asp Ser Glu Arg Gln Tyr Tyr Val Ala Leu Asn Lys Asp Gly
145                 150                 155                 160

Ser Pro Arg Glu Gly Tyr Arg Thr Lys Arg His Gln Lys Phe Thr His
                    165                 170                 175

Phe Leu Pro Arg Pro Val Asp Pro Ser Lys Leu Pro Ser Met Ser Arg
                180                 185                 190

Asp Leu Phe Arg Tyr Arg
                195
```

POLYNUCLEOTIDES ENCODING HEPATOCYTE-SPECIFIC MEMBERS OF THE FGF FAMILY

FIELD OF THE INVENTION

This invention relates to a polypeptide (herein designated referred to as "FGF-16") which is a newly discovered member of the fibroblast growth factor family, as well as to homologs, analogs and derivatives thereof, and to nucleic acid molecules encoding these polypeptides, to methods for the recombinant production thereof, to antibodies raised against the polypeptides, to methods for the use of the polypeptides, and to pharmaceutical compositions of the polypeptides for therapeutic use.

BACKGROUND OF THE INVENTION

The fibroblast growth factor (FGF) family is now known to consist of at least fourteen members, namely, FGF-1to FGF-10 and homologous factors FHF-1 to FHF-4.

FGF-1(aFGF) and FGF-2 (bFGF), which were originally isolated as mitogens for fibroblasts from the brain and the pituitary gland, are widely expressed in developing and adult tissues. These polypeptides exhibit multiple biological activities, including angiogenesis, mitogenesis, cellular differentiation and wound healing; see Baird et al., Cancer Cells, Volume 3, pages 239–243 (1991) and Burgess et al., Annual Review of Biochemistry, Volume 58, pages 575–606 (1989). FGF-3 (also known as "int-2"), FGF-4 (also known as "hst/kFGF"), FGF-5 and FGF-6 were each identified originally as oncogene products: see Dickson et al., Annual Review of the New York Academy of Sciences, Volume 683, pages 18–26 (1991); Yoshida et al., Annual Review of the New York Academy of Sciences, Volume 683, pages 27–37 (1991); Goldfarb et al., Annual Review of the New York Academy of Sciences, Volume 683, pages 38–52 (1991); and Coulier et al., Annual Review of the New York Academy of Sciences, Volume 683, pages 53–61 (1991). FGF-7 (also referred to as "KGF") was isolated as a mitogenic factor for cultured keratinocytes; see Aaronson et al., Annual Review of the New York Academy of Sciences, Volume 683, pages 62–77 (1991). FGF-8 and FGF-9 were isolated as an androgen-induced growth factor and a glial-activating factor from mouse mammary carcinoma cells and human glioma cells, respectively; see Tanaka et al., Proceedings of the National Academy of Sciences USA, Volume 89, pages 8928–8932 (1991) and Miyamoto et al., Molecular Cell Biology, Volume 13, pages 4251–4259 (1993). FGF-10 was identified from rat embryos by homology-based polymerase chain reaction (PCR); see Yamasaki et al., Journal of Biological Chemistry, Volume 271, pages 15918–15921 (1996). These FGFs are expressed predominantly during embryonic development and in some adult tissues.

The four homologous factors (or "FHFs") were identified from the human retina by a combination of random cDNA sequencing, searches of existing sequence data bases and homology-based poylmerase chain reactions; see Smallwood et al., Proceedings of the National Academy of Sciences USA, Volume 93, pages 9850–9857 (1996). These FHFs are expressed predominantly in the developing and mature nervous systems. It has been proposed that FHF-1, FHF-2, FHF-3 and FHF-4 should be designated as FGF-11, FGF-12, FGF-13 and FGF-14, respectively, in accordance with the recommendation of the Nomenclature Committee; see Coulier et al., Journal of Molecular Evolution, Volume 44, pages 43–56 (1997).

SUMMARY OF THE INVENTION

Briefly described, this invention encompasses the discovery and identification of an additional member of the fibroblast growth factor (FGF) family of polypeptides, designated herein as "FGF-16", as well as peptide fragments and analogs thereof, as well as nucleic acid molecules (including degenerate sequences) encoding such polypeptides. Also included within the scope of this invention are chemical (i.e., polymer) derivatives of the polypeptide as well as fragments and analogs composed of alternate sequences of the polypeptide, but having similar biological activity and retaining the same biological function. Additional aspects of the invention comprise vectors and transformed hosts useful for the expression of the nucleic acid molecules and the recombinant production of the polypeptides. As a further aspect, the invention involves the use of the nucleic acid molecules or polypeptides to stimulate the proliferation and development of hepatocytes, both in vitro and in vivo, including the use of the nucleic acids and encoded polypeptides to treat liver disorders.

BRIEF DESCRIPTION OF THE FIGURES

FIGS. 1A–1B. This Figure depicts the nucleic acid sequence of the coding region of the rat cDNA for FGF-16 from nucleotide 17 to nucleotide 637 (SEQ ID NO: 1), and the predicted amino acid sequence of the encoded polypeptide (SEQ ID NO: 2). The start and stop codons in the nucleic acid sequence are underlined. The numbers above individual nucleotides and below individual amino acids refer to the nucleotide and amino acid sequences, respectively.

FIG. 2. This Figure compares the amino acid sequence of rat FGF-16 with that of rat FGF-9 (SEQ ID NO: 3). The numerals refer to the positions of the respective amino acid residues. The asterisks indicate those amino acid residues of FGF-16 and FGF-9 which are identical.

FIGS. 6A–6B. This Figure depicts the nucleotide sequence of the coding region of the full length human cDNA for FGF-16 beginning at nucleotide 23 and ending at nucleotide 643 (SEQ ID NO: 4) and the predicted amino acid sequence of the encoded polypeptide (SEQ ID NO: 5). The start and stop codons in the nucleic acid sequence are underlined.

FIGS. 7A–7D. This Figure, shows BrdU-labeled liver sections from two mice injected with control buffer solution (FIGS. 7A and 7B, respectively), side by side with BrdU-labeled liver sections from two mice injected with a des-34 truncation N-terminal analog of rat FGF-16 ("des-N-34") at a dose of five milligrams per kilogram per day for seven days (FIGS. 7C and 7D, respectively). The comparisons show a significant increase in hepatocellular BrdU labeling in the livers of des-N-34 treated mice.

DETAILED DESCRIPTION OF THE INVENTION

Figure 3:
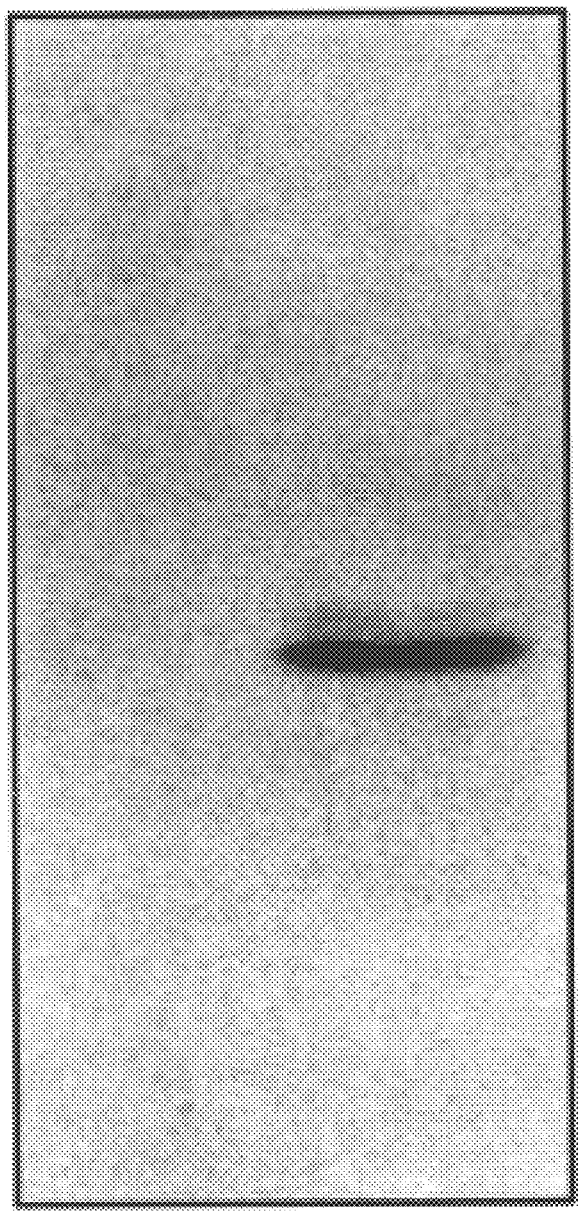
FIG. 3. This Figure shows the detection of recombinant FGF-16 from the cell lysate of Sf9 cells which had been transfected with recombinant baculovirus containing the cDNA for rat FGF-16. The culture medium and cell extracts of the recombinant baculovirus-infected Sf9 cells were subjected to SDS-polyacrylamide gel (12.5%) electrophoresis. Recombinant rat FGF-16 was detected by Western blotting analysis using anti-E tag antibodies. Lane 1, cell lysate; lane 2, culture medium. Prestained Protein Marker Broad Range (New England Biolabs, Beverly, Mass.) was used as the standard for estimating the molecular mass of the polypeptides.

In addition to the polypeptide of FIGS. 1A and 1B (SEQ ID NO: 2) and the polypeptide of FIGS. 6A and 6B (SEQ ID NO: 5), also intended as part of this invention are fragments (i.e, "subsequences"), analogs and derivatives of such polypeptides which are substantially biologically equivalent or share one or more important biological properties, such as hepatocyte growth and proliferation activity. By "substantially biologically equivalent" is meant having the same properties of the polypeptides as described herein, even if in different degree. Preferably, such analogs will cross-react with antibodies raised against the polypeptides of FIGS. 1A–1B and FIGS. 6A–6B. The term "analog" is specifically intended to mean molecules representing one or more amino acid substitutions, deletions and/or additions derived from the linear array of amino acids of the full length polypeptides of FIGS. 1A–1B and 6A–6B, and which are also substantially biologically equivalent or share one or more biological properties.

Especially preferred polypeptide analogs in accordance with this invention are those which possess a degree of homology (i.e., identity of amino acid residues) with the polypeptide of FIGS. 1A–1B (SEQ ID NO: 2) or the polypeptide of FIGS. 6A–6B (SEQ ID NO: 5) in excess of eighty percent (80%), and most preferably, in excess of ninety percent (90%).

Percent sequence identity can be determined by standard methods that are commonly used to compare the similarity in position of the amino acids of two polypeptides in order to generate an optimal alignment of two respective sequences. By way of illustration, using a known computer program such as BLAST or FASTA, two polypeptides are aligned for optimal matching of their respective amino acids (either along the full length of one or both sequences, or along a pre-determined portion of one or both sequences). The programs provide a "default" opening penalty and a "default" gap penalty, and a scoring matrix such as PAM 250. A standard scoring matrix can be used in conjunction with the computer program; see Dayhoff et al., in Atlas of Protein Sequence and Structure, Volume 5, Supplement 3 (1978). The percent identity (or "homology" as used herein) can then be calculated as follows:

$$\frac{\text{Total number of identical matches}}{[\text{No. of residues in region of alignment, not including non-identical residues at either or both ends and residues opposite a gap}]} \times 100$$

Analog polypeptides in accordance with this invention will typically have one or more amino acid substitutions, deletions and/or insertions, as mentioned. Usually, the substitutions will be conservative so as to have little or no effect on the overall net charge, polarity or hydrophobicity of the protein. Examples of conservative substitutions are set forth below.

Conservative Amino Acid Substitutions

Basic: arginine
 lysine
 histidine
Acidic: glutamic acid
 aspartic acid
Polar: glutamine
 asparagine
Hydrophobic: leucine
 isoleucine
 valine
Aromatic: phenylalanine
 tryptophan
 tyrosine
Small: glycine
 alanine
 serine
 threonine
 methionine The polypeptides of this invention may or may not have an amino terminal methionine, depending on the manner in which they are prepared. Typically, an amino terminal methionine residue will be present when the polypeptide is produced recombinantly in a non-secreting bacterial (e.g., *E. coli*) strain as the host.

Polypeptide fragments (i.e., subsequences) included within this invention will be those that have less than the full length sequence, but which possess substantially the same biological activity and are truncated at the amino terminus, the carboxy terminus, and/or internally.

FGF-16 analogs comprising a truncation of amino acids will include those in which one or more amino acid residues are omitted from the full length mature sequence (207 amino acids) starting from the N-terminus up to about amino acid position 35 (referrred to herein as "des-N" analogs). Also contemplated are truncation analogs in which one or more amino acid residues are omitted from the C-terminus up to about amino acid position 19 (referred to herein as "des-C" analogs), including C-terminal truncations in those FGF-16 polypeptides in which amino acid residues have also been omitted from the N-terminus.

When making substitutions or omissions of particular amino acid residues within the naturally occurring (i.e., "native") amino acid sequence of FGF-16, relatively conservative substitutions are preferred so as not to adversely affect desired biological properties to any substantial degree. Thus, for example, residues or regions which are known or suspected to be involved in receptor specificity or heparin binding should generally be avoided if alterations in these sites will detract from these properties. A region believed to be important for receptor binding specificity within FGF-16 extends from tyrosine 147 to tyrosine 161, in both human and rat forms. Sites important for heparin binding (in both rat and human) comprise arginine 68, threonine 69, asparagine 142, asparagine 166, lysine 167, arginine 172, arginine 176, glutamine 181, lysine 182 and phenylalanine 183.

In general, polypeptide analogs, fragments and derivatives in accordance with this invention will be useful for the same purposes for which the polypeptides of SEQ ID NO:

2 and SEQ ID NO: 5 are useful, and in particular as stimulatory factors for the proliferation and growth of hepatocytes in vitro and in vivo.

Nucleic Acids

This invention also encompasses nucleic acid molecules encoding any of the above mentioned polypeptides. Thus, besides the nucleic acid molecules having the particular sequences shown in FIGS. 1A and 1B (SEQ ID NO: 1) and FIGS. 6A and 6B (SEQ ID NO: 4), also included are degenerate nucleic sequences thereof (i.e, differing by one or more bases) encoding the same polypeptide. In addition, this invention encompasses nucleic acid molecules encoding biologically active precursors, fragments and derivatives of the polypeptides described herein. Further, the invention encompasses nucleic acid molecules encoding the complementary (i.e., antisense) strands, as well as nucleic acid molecules which hybridize (or would hybridize but for the variability of nucleotide sequence due to the degeneracy of codons) to the nucleic acid molecules of FIGS. 1A–1B or FIGS. 6A–6B, or to fragments or degenerate sequences thereof or their complementary strands, preferably under relatively stringent conditions (for example, conditions such as described below). The present invention also embraces nucleic acid molecules that may encode additional amino acid residues flanking the 5' or 3' portions of the region encoding the "mature" polypeptide (that is, the processed product harvested from the host), such as sequences encoding alternative pre/pro regions (that is, sequences responsible for secretion of the polypeptide through cell membranes) in place of the "native" pre/pro regions. The additional sequences may also constitute noncoding sequences, including regulatory sequences such as promoters of transcription or translation, depending on the host cell. The nucleic acid molecules may even include various internal non-coding sequences (introns) known to occur within genes.

In general, as employed herein the term "stringent conditions" refers to hybridization and washing under conditions that permit the binding of a nucleic acid molecule such as an oligonucleotide or cDNA molecule to highly homologous sequences.

One stringent washing solution, suitable for use with cDNA probes at a temperature of 55–65° C., is composed of 0.015M sodium chloride, 0.0015M sodium citrate (0.1× SSC, where 1× SSC=0.15M sodium chloride and 0.015M sodium citrate) and 0.1 percent SDS. Another, slightly less stringent washing solution, is composed of 0.2× SSC and 0.1 percent SDS, and can be used at temperature between 50 and 65° C.

Where oligonucleotide probes are used to screen cDNA or genomic libraries, the following stringent washing conditions may be used. One protocol uses 6× SSC with 0.05 percent sodium pyrophosphate at a temperature of 35–62° C., depending on the length of the oligonucleotide probe. For example, 14-base pair probes are washed at 35–40° C., 17-base pair probes are washed at 45–50° C., 20-base pair probes are washed at 52–57° C., and 23-base pair probes are washed at 57–63° C. The temperature can be increased 2–6° C. where background non-specific binding appears to be high. Another protocol utilizes tetramethylammonium chloride (TMAC) for washing oligonucleotide probes. A suitable stringent washing solution is composed of 3M TMAC, 50 mM Tris-HCl, pH 8.0, and 0.2 percent SDS. The washing temperature for use with this solution is a function of the length of the probe. For example, a 17-base pair probe is typically washed at about 45–50° C.

Also included within the scope of this invention are RNA molecules that are homologous to any of the aforementioned DNA molecules.

Recombinant Expression

The polypeptides of the invention can be prepared using well known recombinant technology methods such as those set forth in Sambrook et al., Molecular Cloning: A Laboratory Manual, Cold Spring Harbor Laboratory Press, Cold Spring Harbor, N.Y. (1989) and/or Ausubel et al., Editors, Current Protocols in Molecular Biology, Green Publishers Inc. and Wiley and Sons, New York (1994). A gene or cDNA encoding the polypeptide or truncated version thereof may be obtained, for example, by screening a genomic or cDNA library, or by PCR amplification. Alternatively, a DNA molecule encoding the polypeptide may be prepared by chemical synthesis using methods well known to the skilled artisan, such as those described by Engels et al. in Angew. Chem. Intl. Ed., Volume 28, pages 716–734 (1989). Typically, the DNA encoding the polypeptide will be several hundred nucleotides in length. Nucleic acids larger than about one hundred nucleotides can be synthesized as several fragments using these same methods, and the fragments can then be ligated together to form a nucleotide sequence of the desired length.

The nucleic acid molecules of this invention (whether genes or cDNAs) can be inserted into an appropriate expression vector for expression in a suitable host organism or cell using recombinant methods. The vector is selected to be functional in the particular host employed (i.e., the vector is compatible with the host cell machinery, such that amplification and/or expression of the gene can occur). The polypeptide, fragment or analog may be amplified/expressed in prokaryotic, yeast, insect (baculovirus systems) and/or eukaryotic host cells, or in transgenic non-human animal species as the host. Selection of the host cell will depend at least in part on whether the polypeptide expression product is to be glycosylated. If glycosylation is desired, then yeast, insect or mammalian host cells are preferred for use, in that yeast cells will glycosylate the polypeptide, and insect and mammalian cells can glycosylate and/or phosphorylate the polypeptide in a manner similar to "native" glycosylation and/or phosphorylation.

The vectors used in any of the host cells to express the polypeptide may also contain a 5' flanking sequence (also referred to as a "promoter") and other expression regulatory elements operatively linked to the nucleic acid molecule (DNA) to be expressed, as well as enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below.

Optionally, the vector may also contain a "tag" sequence, i.e., an oligonucleotide sequence located at the 5' or 3' end of the polypeptide-coding sequence that encodes polyHis (such as hexaHis) or another small immunogenic sequence. This tag will be expressed along with the protein, and can serve as an affinity tag for purification of the polypeptide from the host cell. Optionally, the tag can subsequently be removed from the purified polypeptide by various means, for example, with use of a selective peptidase.

The 5' flanking sequence may be the native 5' flanking sequence, or it may be homologous (i.e., from the same species and/or strain as the host), heterologous (i.e., from a species other than the host cell species or strain), hybrid (i.e., a combination of 5' flanking sequences from more than one source), or synthetic. The source of the 5' flanking sequence may be any unicellular prokaryotic or eukaryotic organism, any vertebrate or invertebrate organism, or any plant, provided that the 5' flanking sequence is functional in, and can be activated by the host cell machinery.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, or by other methods known to the skilled artisan. Selection of suitable enzymes to accomplish this purpose will be readily apparent to one skilled in the art.

The origin of replication element is typically a part of prokaryotic expression vectors purchased commercially, and which aids in the amplification of the vector in a host cell. Amplification of the vector to a certain copy number can, in some cases, be important for optimal expression of the polypeptide. If the vector of choice does not contain an origin of replication site, one may be chemically synthesized based on a known sequence and then ligated into the vector.

The transcription termination element is typically located 3' to the end of the polypeptide coding sequence and serves to terminate transcription of the polypeptide. Usually, the transcription termination element in prokaryotic cells is a G-C rich fragment followed by a poly-T sequence. While the element is easily cloned from a library or even purchased commercially as part of a vector, it can also be readily synthesized using methods for nucleic acid synthesis such as those referred to above.

A selectable marker gene element encodes a protein necessary for the survival and growth of a host cell grown in a selective culture medium. Typical selection marker genes encode proteins that (a) confer resistance to antibiotics or other toxins, for example, ampicillin, tetracycline or kanamycin for prokaryotic host cells, (b) complement auxotrophic deficiencies of the cell, or (c) supply critical nutrients not available from complex media. Preferred selectable markers are the kanamycin resistance gene, the ampicillin resistance gene and the tetracycline resistance gene.

The ribosome binding element, commonly called the Shine-Dalgarno sequence (for prokaryotes) or the Kozak sequence (for eukaryotes), is necessary for the initiation of translation for mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for the polypeptide to be secreted from the host cell, a signal sequence may be used to direct the polypeptide out of the host cell where it is synthesized. Typically, the signal sequence is positioned in the coding region of nucleic acid sequence, or directly at the 5' end of the coding region. Many signal sequences have been identified, and any of them that are functional in the selected host cell may be used here. Consequently, the signal sequence may be homologous or heterologous to the polypeptide. Additionally, the signal sequence may be chemically synthesized using methods such as those referred to set above.

Host cells may be prokaryotic host cells (such as $E.\ coli$) or eukaryotic host cells (such as yeast, insect or vertebrate cells). The host cell, when cultured under suitable nutrient conditions, can synthesize the polypeptide, which can subsequently be collected by isolation from the culture medium (if the host cell secretes it into the medium) or directly from the host cell producing it (if not secreted). After collection, the polypeptide can be purified using methods such as molecular sieve chromatography, affinity chromatography, and the like. In general, if the polypeptide is expressed in $E.\ coli$ it will contain a methionine residue at the N-terminus in its recovered form (i.e., $Met^{31\ 1}$), unless expressed in a strain of $E.\ coli$ in which the methionine is enzymatically cleaved off by the host.

Suitable cells or cell lines may also be animal cells, and especially mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or they may contain a dominantly acting selection gene. Still other suitable mammalian cell lines include but are not limited to, HeLa, mouse L-929 cells, 3T3 lines derived from Swiss, Balb-c or NIH mice, BHK or HaK hamster cell lines.

Insertion (also referred to as "transformation" or "transfection") of the vector into the selected host cell may be accomplished using calcium chloride, electroporation, microinjection, lipofection or the DEAE-dextran method. The particular method selected will, in part, depend on the type of host cell to be used. These methods and other suitable methods are well known to the skilled artisan. See, for example, Sambrook et al., above.

The host cells containing the vector may be cultured using standard media well known to the skilled artisan. The media will usually contain all of the nutrients necessary for the growth and survival of the transformed cells. Suitable media for culturing $E.\ coli$ cells are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for the culturing of insect cells is Grace's medium supplemented with yeastolate, lactalbumin hydrolysate and/or fetal calf serum, as necessary.

Typically, an antibiotic or other compound useful for selective growth of the transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the polypeptide has been designed to be secreted from the host cells, the majority of polypeptide will likely be found in the cell culture medium. If, on the other hand, the polypeptide is not secreted, it will be present in the cytoplasm (for eukaryotic, Gram-positive bacteria and insect host cells) or in the periplasm (for Gram-negative bacteria host cells).

For intracellular polypeptide, the host cells are typically first disrupted mechanically or osmotically to release the cytoplasmic contents into a buffered solution. The polypeptide is then isolated from this solution. Purification of the polypeptide from solution can thereafter be accomplished using a variety of techniques. If the polypeptide has been synthesized to contain a tag such as Hexahistidine or other small peptide at either the carboxyl or amino terminus, it may be purified in a one-step process by passing the solution through an affinity column in which the column matrix has a high affinity for the tag or for the polypeptide directly (i.e., a monoclonal antibody). For example, polyhistidine binds with great affinity and specificity to nickel, thus an affinity column of nickel (such as the Qiagen nickel columns) can be used for purification. (See, for example, Ausubel et al., eds., Current Protocols in Molecular Biology, John Wiley & Sons, New York, 1994).

Where, on the other hand, the polypeptide has no tag and no antibodies are available, other well known procedures for purification can be used. Such procedures include, without limitation, ion exchange chromatography, molecular sieve chromatography, hydrophobic interaction chromatography, reverse-phase chromatography, native gel electrophoresis in combination with gel elution, and preparative isoelectric focusing. These operations can be performed in HPLC or low pressure modes. In some cases, two or more of these techniques may be combined to achieve increased purity.

If it is anticipated that the polypeptide will be found primarily in the periplasmic space of the bacteria or the cytoplasm of eukaryotic cells, the contents of the periplasm or cytoplasm, including inclusion bodies (e.g., Gram-negative bacteria) if the processed polypeptide has formed such complexes, can be extracted from the host cell using any standard technique known to the skilled artisan. For example, the host cells can be lysed to release the contents of the periplasm by the use of a French press, homogenization and/or sonication. The homogenate can then be centrifuged.

Other Modes of DNA Expression

In addition to typical methods of recombinant expression in heterologous hosts such as just described, the polypeptides of this invention may be expressed by other known means, which may or may not involve the use of expression vectors.

For instance, techniques of homologous recombination may be employed to facilitate expression of a polypeptide of this invention, without the use of an expression vector. By way of illustration, a suitable DNA construct, comprising a regulatory element, can be inserted into the genome of a cell by homologous recombination such that it is in close proximity to an endogenous gene segment encoding FGF-16 and stimulates the expression thereof in situ. See U.S. Pat. No. 5,272,071 (Chappel). The polypeptide expression product is then harvested and purified and can be used in the same manner as polypeptides produced by recombinant expression in a heterologous host.

Alternatively, the isolated nucleic acid molecules described herein may be used directly in cell or gene therapy applications. Vectors suitable for gene therapy, such as retroviral or adenoviral vectors, are known and can be modified to incorporate nucleic acid encoding the polypeptide of the present invention for administration to the patient and expression in a desired location in vivo. See, for instance, Verma, Scientific American, pages 68–84 (November, 1990). In these situations, genomic DNA, cDNA, and/or synthetic DNA encoding the polypeptide or a fragment or variant thereof may be operably linked to a constitutive or inducible promoter which is active in the tissue in which expression is desired, then inserted into a suitable vector. In one particular method of application, cells are removed from the patient, transfected with the gene therapy vector using standard transfection procedures for eukaryotic cells, and tested for polypeptide production and secretion. Such cells can be liver cells, bone marrow cells, cells derived from the umbilical cord or blood progenitor cells, for instance. Alternatively, the cells can be pretreated with a DNA regulatory element or segment to activate via homologous recombination for the genomic expression of an endogenous DNA molecule encoding the polypeptide in the manner described above. Those cells expressing and secreting the polypeptide can then be re-introduced into the patient such that they are viable and function as a localized source of the polypeptide in situ. The cellular delivery may be regulated to endure for a preselected period of time, such as days, weeks or months, at the end of which the recipient may receive another "dose" (that is, a fresh transplantation of polypeptide-secreting cells).

Other methods can involve the targeted delivery of DNA constructs directly to tissues or organs in the body for in situ expression of therapeutically effective amounts, such as described in greater detail further below.

Polypeptide Derivatives

Chemically modified polypeptides, in which the polypeptide is linked to a polymer in order to modify properties (referred to herein as "derivatives"), are included within the scope of the present invention. The polymer is typically water soluble so that the protein to which it is attached does not precipitate in an aqueous environment, such as a physiological environment. The polymer may have a single reactive group, such as an active ester for acylation or an aldehyde for alkylation, so that the degree of polymerization may be controlled. A preferred reactive aldehyde is polyethylene glycol propionaldehyde, which is water stable, or mono C1–C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. By way of illustration, the water soluble polymer, or mixture thereof if desired, may be selected from the group consisting of polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

Pharmaceutical Compositions

For therapeutic purposes, the polypeptides of this invention, or fragments, analogs or derivatives thereof, will typically be formulated into suitable pharmaceutical compositions adapted for therapeutic delivery, which constitutes an additional aspect of this invention. Such pharmaceutical compositions will typically comprise an effective amount of the polypeptide (or fragment, analog or derivative), alone or together with one or more carriers, excipients or other standard ingredients for a pharmaceutical composition. By "effective amount" is meant an amount sufficient to produce a measurable biological effect on the treated cells or organ, such as the proliferation or growth of hepatocytes or regeneration of liver tissue (see below for further details). The carrier material may be water for injection, preferably supplemented with other materials common in solutions for administration to mammals. Typically, the polypeptide will be administered in the form of a composition comprising a purified form of the polypeptide (which may be chemically modified) in conjunction with one or more physiologically acceptable carriers, excipients, or diluents. Neutral buffered saline or saline mixed with serum albumin are exemplary appropriate carriers. Other standard carriers, diluents, and excipients may be included as desired.

The pharmaceutical compositions may be prepared for storage by mixing the selected composition having the desired degree of purity with optional physiologically acceptable carriers, excipients or stabilizers (Remington's Pharmaceutical Sciences, 18th edition, A. R. Gennaro, ed., Mack Publishing Company, 1990) in the form of a lyophilized cake or an aqueous solution. Acceptable carriers, excipients or stabilizers are nontoxic to recipients and are preferably inert at the dosages and concentrations employed, and include buffers such as phosphate, citrate, acetate, succinate or other organic acid salts; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, sucrose, lactose or dextrins; chelating agents such as EDTA; sugar alcohols such as mannitol or sorbitol; salt-forming counterions such as sodium; and/or nonionic surfactants such as Tween or Pluronics.

Any composition of this invention which is intended to be used for in vivo administration must be sterile. Sterilization is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Preferred Stabilizing Agents

The stability of the polypeptides of this invention below, at or about room temperature in buffered solution may be enhanced, and any tendnency toward protein aggregation lessened, by the addition of an organic or inorganic sulfate (for example, sodium sulfate or ammonium sulfate) and EDTA. Preferably, the sulfate salt is employed in an amount of about 10 mM or more, and the EDTA in an amount from about 1 $\mu$M to about 10 mM.

Dosages and Routes of Administration

The amount of polypeptide that will be effective in the treatment of a particular disorder or condition will depend on the nature of the polypeptide and disorder or condition, as well as the age and general health of the recipient, and can be determined by standard clinical procedures. Where possible, it will be desirable to determine the dose-response curve of the pharmaceutical composition first in vitro, as in bioassay systems, and then in useful animal model systems in vivo prior to testing in humans. In general, suitable in vivo amounts can be developed based on a knowledge of the therapeutically effective doses known for the wild type protein on which the analogs are based. The skilled practitioner, considering the therapeutic context, type of disorder under treatment, and other applicable factors, will be able to ascertain proper dosing without undue effort. For in vivo administration to humans, it is anticipated that amounts in the range between about thirty micrograms and about three hundred micrograms per kilogram of body weight per day will be adequate. Typically, a practitioner will administer the polypeptide composition until a dosage is reached that achieves the desired effect. The composition may be administered as a single dose, or as two or more doses (which may or may not contain the same amount of polypeptide) over time, or on a continuous basis.

The route of administration of the therapeutically active polypeptides or pharmaceutical compositions of the polypeptides can be in accordance with any of the known methods, such as oral or by injection or infusion by intravenous (or intraarterial), intraperitoneal, or intralesional routes, or by the use of sustained release systems or implantation. Where desired, the compositions may be administered continuously by infusion, bolus injection or by implantation device. Alternatively or additionally, the polypeptides of this invention may be administered locally via implantation into the affected area of a membrane, sponge, or other appropriate material onto which the polypeptide has been absorbed. Where an implantation device is used, the device may be implanted into any suitable tissue or organ.

The polypeptides of this invention may also be administered in a sustained release formulation or preparation. Suitable examples of sustained release preparations include semipermeable polymer matrices in the form of shaped articles, for example, films or microcapsules. Sustained release matrices include polyesters, hydrogels, polylactides (U.S. Pat. No. 3,773,919), copolymers of L-glutamic acid and gamma ethyl-L-glutamine (Sidman et al, Biopolymers, Volume 22, pages 547–556, 1983), poly (2-hydroxyethylmethacrylate) (Langer et al., J. Biomed. Mater. Res., Volume 15, pages 167–277, 1981, and Langer, Chem. Tech., Volume 12, pages 98–105, 1982), ethylene vinyl acetate (Langer et al., above) or poly-D(–)-3-hydroxybutyric acid. Sustained-release compositions also may include liposomes, which can be prepared by any of several methods known in the art; see, for example, Epstein et al., Proc. Natl. Acad. Sci. USA, Volume 82, pages 3688–3692 (1985), and Hwang et al., Proc. Natl. Acad. Sci. USA, Volume 77, pages 4030–4034 (1980).

Gene and Cell Therapy Applications

In certain situations, it may be desirable to use so-called gene or cell therapy methods for administration. Such a form of delivery may be particularly effective for the in vivo stimulation of hepatocyte proliferation in the liver. In these situations, genomic DNA, cDNA and/or synthetic DNA encoding the polypeptide or a fragment or variant thereof may be operably linked to a constitutive or inducible promoter which is active in the tissue into which the composition will be injected. This construct can then be inserted into a suitable vector such as an adenovirus vector or a retrovirus vector to create a gene therapy vector. The cells of the patient to be treated can be removed from the patient, transfected with the gene therapy vector using standard transfection procedures for eukaryotic cells, and tested for polypeptide production and secretion. Those cells expressing and secreting the polypeptide can then be re-introduced into the patient such that they are viable and function as a localized source of the polypeptide in situ.

Alternatively, the DNA construct may be directly injected into the tissue of the organ to be treated, where it can be taken up in vivo and expressed locally in the cells, provided that the DNA is operable linked to a promoter that is active in such tissue. The DNA construct may also additionally include vector sequence from such vectors as an adenovirus vector, a retroviral vector and/or a herpes virus vector, to aid uptake in the cells. For the in vivo regeneration of hepatocytes in the liver, the use of Moloney retroviral vectors may be especially effective; see Bosch et al., Journal of Clinical Investigation, Volume 98, Number 12, pages 2683–2687 (1966). The vector/DNA construct may be mixed with a pharmaceutically acceptable carrier or carriers for injection.

Antibody Formation and Diagnostic Applications

The polypeptides of this invention can also be used in accordance with standard procedures to generate antibodies which are useful for medically related purposes. In particular, such antibodies, preferably in labeled form, will be useful for both in vivo and in vitro diagnostic purposes to detect the presence of the polypeptides in a fluid or tissue sample, for example.

Various procedures known in the art can be employed for the production of polyclonal antibodies that recognize epitopes of the polypeptides. For the production of antibody, various host animals can be immunized by injection with an analog polypeptide, or fragment or derivative thereof, including but not limited to rabbits, mice, rats, etc. Various adjuvants may be used to increase the immunological response, depending on the host species, including but not limited to Freund's, mineral gels such as aluminum hydroxide (alum), surface active substances such as lysolecithin, pluronic polyols, polyanions, peptides, oil emulsions, keyhole limpet hemocyanins, dinitrophenol, and potentially useful human adjuvants such as Bacille Calmette-Guerin and *Corynebacterium parvum*.

For the preparation of monoclonal antibodies directed toward the polypeptides, any technique which provides for the production of antibody molecules by continuous cell lines in culture may be used. For example, the hybridoma technique originally developed by Kohler and Milstein and described in Nature, Volume 256, pages 495–497 (1975), as well as the trioma technique, the human B-cell hybridoma technique described by Kozbor et al. in Immunology Today, Volume 4, page 72 (1983), and the EBV-hybridoma technique to produce monoclonal antibodies described by Cole et al in "Monoclonal Antibodies and Cancer Therapy", Alan R. Liss, Inc., pages 77–96 (1985), are all useful for preparation of monoclonal antibodies.

In addition, a molecular clone of an antibody to an epitope or epitopes of the polypeptide can be prepared with known techniques. In particular, recombinant DNA methodology may be used to construct nucleic acid sequences which encode a monoclonal antibody molecule or antigen-binding region thereof; see, for example, Maniatis et al., Molecular Cloning, A Laboratory Manual, Cold Spring Harbor Laboratory, Cold Spring Harbor, N.Y. (1982).

DESCRIPTION OF SPECIFIC EMBODIMENTS

The invention is described in further detail with regard to the following materials, methods and procedures, which are meant to be illustrative only and are not intended to be limiting.

I. Preparation of RNA from Rat Embryos and Adult Tissues

RNA was prepared from Wistar rat (male) tissues using a commercially available RNA extraction kit (Pharmacia Biotech, Uppsala, Sweden). Poly $(A)^+$ RNA was prepared using oligo(dT)-cellulose (Type 2, Collaborative Biomedical Products, Bedford, Mass.).

II. Isolation and Analysis of Rat FGF Family cDNAs

Five micrograms of Rat brain poly $(A)^+$ RNA was incubated for sixty minutes at 37° C. in twenty microliters ($\mu$l) of a reaction mixture containing three hundred units of Moloney murine leukemia virus reverse transcriptase (GIBCO-BRL, Gaithersburg, Md.), fifteen units of human placenta RNase inhibitor (Wako Pure Chemicals, Osaka, Japan) and one-half microgram ($\mu$g) of a random hexadeoxynucleotide primer. To amplify the FGF family cDNAs, PCR was performed for thirty cycles in twenty five microliters of a reaction mixture containing an aliquot of the above cDNA solution, 0.05 unit per microliter (unit/$\mu$l) of Taq DNA polymerase (Wako Pure Chemicals) and five picomole per microliter (pmole/$\mu$l) of each of the sense and antisense degenerate primers representing all possible codons corresponding to the consensus amino acid sequences of mouse FGF-3 and FGF-7, YLAMNK and YNTYAS, respectively ; see Moore et al., EMBO Journal, Volume 5, pages 919–924 (1986) and Mason et al., Mech. Dev., Volume 45, pages 15–30 (1994). The amplified DNA of expected size (approximately 110 base pairs) was cloned into the pGEM-T DNA vector (Promega, Madison, Wis.). The nucleotide sequence of the cloned DNA was determined by a DNA sequencer (Applied Biosystems, Foster, Calif.). To determine the entire coding region, cDNA synthesized from rat heart poly $(A)^+$ RNA was analyzed by the Rapid Amplification of cDNA Ends (RACE) method; Frohman et al., Proceedings of the National Academy of Sciences USA, Volume 78, pages 3824–3828 (1988). The cDNA covering the entire coding region was amplified by PCR (twenty five cycles) in a reaction mixture containing an aliquot of the rat heart cDNA solution, 0.05 unit/$\mu$l Ex Taq DNA polymerase (TaKaRa, Kyoto, Japan) and 0.4 pmole/$\mu$l of each of the sense and antisense primers for its 5' and 3' non-coding regions, and it was then cloned into the pGEM-T DNA vector.

III. Expression of rat FGF-16 cDNA in Sf9 Cells

An FGF-16 cDNA with a DNA fragment (75 base pairs) encoding an E tag (GAPVPYPDPLEPR) (SEQ ID NO: 6) and a 6XHis tag (HHHHHH) at the 3' terminus of the coding region was constructed in the transfer vector DNA, pBacPAK9 (Clontech, Palo Alto, Calif.). Recombinant baculovirus containing the FGF-16 cDNA with the tag sequences was obtained by co-transfection of Sf9 cells with the recombinant pBacPAK9 and a Bsu36 I-digested expression vector (Promega). Sf9 cells were infected with the resultant recombinant baculovirus to produce recombinant FGF-16 with the tags.

IV. Detection of Recombinant rat FGF-16 by Western Blotting Analysis

The culture supernatant and cell lysate of Sf9 cells infected with the recombinant baculovirus were subjected to sodium dodecyl sulfate (SDS)-polyacrylamide gel (12.5%) electrophoresis under reducing conditions, then transferred onto a nitrocellulose membrane (Hybond-ECL, Amersham, Buckinghamshire, England). The membrane was then incubated with phosphate-buffered saline (PBS) containing 0.1% Tween 20 and 5% nonfat dry milk. Incubation was conducted for one hour at room temperature with anti-E tag antibodies (Pharmacia Biotech) in PBS containing 0.1% Tween 20 (PBS-T). After washing in PBS-T, the membrane was treated for one hour at room temperature with goat anti-rabbit immunoglobulin G conjugated to horseradish peroxidase (Cappel, Durham, N.C.). The membrane was washed four times in PBS-T and reacted with chemiluminescent horseradish peroxidase substrate (Amersham). The protein with the E tag was visualized by exposure of the membrane to X-ray film (RX Medical, Fuji Photo Film Co., Tokyo, Japan).

V. Northern Blotting Analysis

Aliquots of RNA (10 $\mu$g each) from rat tissues were dissolved on a denaturing agarose gel (1%) containing formaldehyde, and then transferred to a nitrocellulose membrane in 20× SSC (1× SSC: 0.15M NaCl/0.015M sodium citrate) overnight. The membrane was then baked at 80° C. for two hours under a vacuum, then prehybridized at 60° C. for four hours in hybridization solution (5× SSC/0.1% sodium dodecyl sulfate (SDS)/4× Denhardt's solution/100 $\mu$g/ml heat-denatured salmon sperm DNA/5% sodium dextran sulfate), and followed by hybridization at 60° C. for eighteen hours in a hybridization solution containing a $^{32}$P-labeled FGF-16 cDNA probe labeled by a random primer labeling kit (TaKaRa) with deoxycytidine 5'-[α-$^{32}$P] triphosphate (approximately 110 TBq/mmol) (ICN Biomedicals Inc., Costa Mesa, Calif.). The membrane was then washed at room temperature three times, for twenty minutes each time, in 1× SSC and 0.1% SDS, and twice at 60° C. in 0.2× SSC and 0.1% SDS. The washed membrane was analyzed with a radio-imaging analyzer (BAS 2000, Fuji Photo Film Co.).

VI. In Situ Hybridization

Wistar rat embryos (E19) were frozen in powdered dry ice. Sagittal sections were cut at sixteen micrometers (μm) by a cryostat, then thaw-mounted onto polylysine-coated slides, and stored at −85° C. until hybridization. $^{35}$S-labeled rat FGF-16 antisense and sense cRNA probes were transcribed using SP6 RNA polymerase and T7 RNA polymerase (TaKaRa) with uridine 5'-α{$^{35}$S}thiotriphosphate (approximately 30 TBq/mmol) (Amersham), respectively. The sections were examined by in situ hybridization with the labeled probe as described in Yamasaki et al., above. To determine the regional localization of the rat FGF mRNA, labeled sections were exposed to X-ray film (Hyperfilm-β max, Amersham). The sections were visualized by counterstaining with hematoxylin and eosin.

VII. Isolation of the cDNA Encoding rat FGF-16

Members of the FGF family have a conserved core region, as noted above. Thus, for instance, amino acid residues 96 to 101 (YLAMNK) and 126 to 131 (YNTYAS) of FGF-3 are identical with those of the corresponding regions of FGF-7: see also Moore et al. and Mason et al., above. Accordingly, degenerate oligonucleotide primers representing all possible codons corresponding to the consensus sequences of FGF-3 and FGF-7 were designed to isolate, by polymerase chain reaction (PCR), cDNA fragments encoding novel members of the FGF family. A cDNA fragment encoding a novel member of the FGF family, FGF-10, was previously isolated from rat embryos by PCR using these same primers: see Yamasaki et al., above. The amino acid sequence of FGF-10 is most highly homologous (60%) to the amino acid sequences of FGF-3 and FGF-7.

FGFs are abundantly present in the brain as well as in embryos; see Baird et al. and Burgess et al., above. Consequently, an attempt was made to isolate cDNA fragments encoding novel members of the FGF family from the rat brain by PCR using the consensus primers described above. cDNA synthesized from rat brain poly(A)$^+$ RNA was amplified by PCR using the primers. DNA of expected size (approximately 110 base pairs), which was a major amplified product, was cloned. Fifty-five clones were isolated and their nucleotide sequences were determined. Forty-seven clones were found to be FGF-related cDNA clones. Among them, thirty-three clones had sequences identical to that of the rat FGF-10 cDNA and nine clones had sequences identical to that of FGF-7 cDNA. Four clones had a sequence highly homologous to that of the mouse FGF-3 cDNA, indicating that they were rat FGF-3 cDNAs. Only one clone had a sequence similar but not identical to those of the cDNAs encoding known members of the FGF family, suggesting that this cDNA encoded a novel member of the FGF family.

The expression of the mRNA encoding this FGF found in adult rat tissue was preliminarily examined by PCR with primers specific for the mRNA. The data indicated that the mRNA was expressed in the heart much more abundantly than in the brain. The cDNA covering the entire coding region of the FGF was isolated from the heart by the Rapid Amplification of cDNA Ends (RACE) method; see Frohman et al., cited above.

VIII. Structure of Rat FGF-16

The nucleotide sequence of the coding region of the cDNA allowed elucidation of the complete 207-amino acid long sequence of a rat FGF polypeptide (SEQ ID NO:2), which contains a conserved amino acid core of about one hundred and twenty amino acids (i.e., amino acids 58–149 and 161–189). The full length sequence for this rat FGF is set forth in FIGS. 1A and 1B. The cDNA fragment was originally amplified by homology-based PCR with primers for the consensus amino acid sequences of FGF-3 and FGF-7. Although one consensus sequence, YNTYAS, was found at amino acids 144 to 149 of the polypeptide, another consensus sequence, YLAMNK, was not found. However, a sequence similar to the latter consensus sequence was found at amino acids 114 to 119: YLGMNE (see FIGS. 1A–1B). This result indicates that the cDNA fragment was amplified from the brain cDNA by PCR with a mismatched primer.

Two cysteine residues that are well conserved in other memebers of the FGF family are also conserved in this rat FGF polypeptide (specifically, amino acids 67 and 133). Because this polypeptide is the sixteenth documented member of the FGF family, it is now tentatively designated herein as "FGF-16". The amino acid sequence of FGF-16 is found to be most highly homologous (73%) to that of FGF-9 (see FIG. 2). Hydropathy plot analysis confirmed the low hydrophobicity of the amino-terminal region of FGF-16, similar to FGF-9, indicating that FGF-16 has no typical signal sequence; see Hopp and Woods, Proceedings of the National Academy of Sciences USA, Volume 78, pages 3824–3828 (1991).

IX. Expression of Rat FGF-16 cDNA in Sf9 Cells

FGF-3, FGF-4, FGF-5, FGF-6, FGF-7 and FGF-8, with typical signal sequences at their amino termini, are known to be efficiently secreted from cells; see Tanaka et al., Dickson et al., Yoshida et al., Goldfarb et al. and Coulier et al., above. In contrast, FGF-1, FGF-2, FGF-9 and FHF-1 to FHF-4 have no typical signal sequence at their amino termini; see Baird et al., Burgess et al., Miyamoto et al. and Smallwood et al., above. FGF-1, FGF-2 and FHF-1 to FHF-4 are not secreted. In contrast, however, FGF-9 is efficiently secreted despite the absence of a typical signal sequence.

To examine whether FGF-16 is secreted, Sf9 cells were infected with recombinant baculovirus containing rat FGF-16 cDNA with the 3' terminal extension encoding E and 6XHis tags. To detect recombinant FGF-16 with a carboxyterminal 25-amino acid extension of the tags, both the culture supernatant and cell lysate were examined by Western blotting analysis using anti-E tag antibodies. A major band of approximately 26 kilodaltons was detected chiefly in the culture supernatant (see FIG. 3). The observed molecular mass of the major band was consistent with the calculated molecular mass of recombinant FGF-16 (i.e., 26,462 daltons). The 26-kilodalton protein was purified by affinity chromatography using a chelating column, and then subjected to amino acid sequence determination using a commercial protein sequencer. The aminoterminal sequence could not be determined, however, which indicates that the amino-terminal amino acid is probably blocked.

X. Expression of Rat FGF-16 mRNA in Adult Rat Tissues

Figure 4:
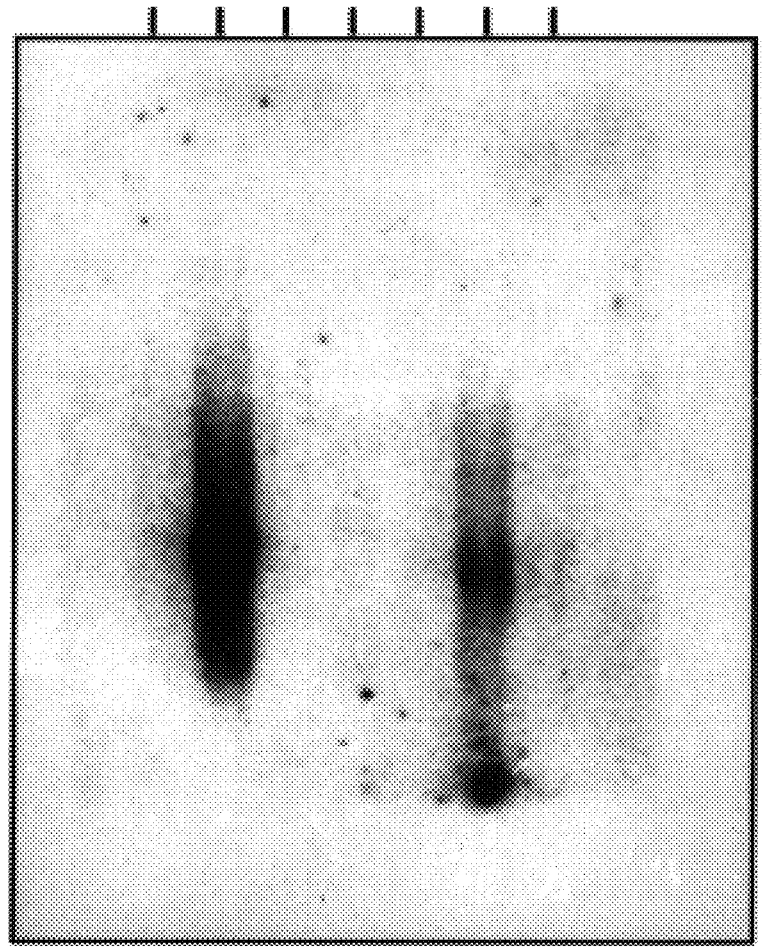
FIG. 4. This Figure shows the expression of mRNA for rat FGF-16 in various adult tissues. Aliquots of RNA (10 μg each) were electrophoresed on a denaturing agarose gel (1%) containing formaldehyde, and then transferred onto a nitrocellulose membrane. Hybridization was performed with a $^{32}$P-labeled rat FGF-16 cDNA probe. The positions of 28S and 18S RNAs are indicated as "28S" and "18S", respectively. Lanes "Br", "He", "Lu", "Li", "Ki", "BA" and "WA" indicate mRNA from the adult brain, heart, lung, liver, kidney, brown adipose tissue and white adipose tissue, respectively.

The expression of FGF-16 mRNA in adult rat tissues was investigated in the following manner:

RNA from the brain, heart, lung, liver, kidney, brown adipose tissue and white adipose tissue was examined by Northern blotting analysis using a $^{32}$P-labeled FGF-16 cDNA probe. The integrity of RNA was confirmed by electrophoresis on a denaturing agarose gel containing formaldehyde. The labeled probe strongly hybridized to a mRNA of 1.8 kilobases in the heart (see FIG. 4). The labeled mRNA was also moderately detected in the brown adipose tissue. However, the mRNA was not detected in the brain, lung, liver, kidney and white adipose tissue. The expression of FGF-16 mRNA in other tissues was also examined, including the small intestine, muscle, thymus, stomach, pancreas, spleen and testis by PCR with specific primers for rat FGF-16 mRNA. FGF-16 mRNA was detected in these tissues at much lower levels than in the heart. Thus, FGF-16 mRNA is predominantly expressed in the heart and brown adipose tissue.

XI. Expression of Rat FGF-16 mRNA in the Rat Embryo

Figure 5A:
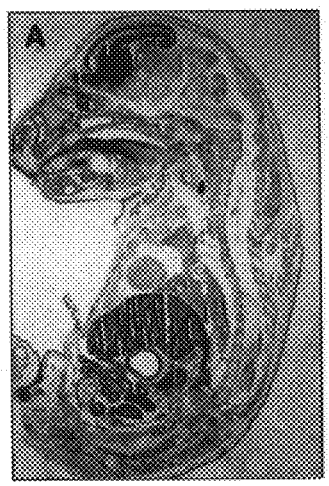
FIGS. 5A–5C. This Figure, depicts the localization of mRNA for FGF-16 in a sagittal section of a rat embryo (E19). The sagittal section was hybridized with a $^{35}$S-labeled antisense (FIG. 5B) or sense (FIG. 5C) FGF-16 cRNA probe. The section was also counterstained with hemaoxylin and eosin (FIG. 5A). The markings "He" and "BA" indicate heart tissue and brown adipose tissue, respectively.
Figure 5B:
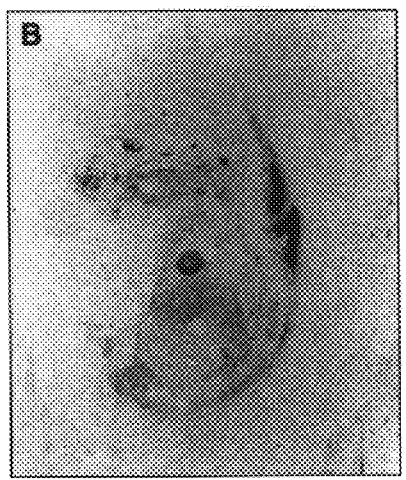
Figure 5C:

To examine the expression of FGF-16 mRNA in the embryo (E19), sagittal sections of embryos were analyzed by in situ hybridization with a $^{35}$S-labeled antisense or sense FGF-16 cRNA probe, followed by macroautoradiography. With the antisense probe, discrete labeling was also observed in the brown adipose tissue and heart of the embryo (FIG. 5B). However, no labeling was observed with the sense probe as a control (FIG. 5C). These results indicate that FGF-16 mRNA in the embryo is also predominantly expressed in the heart and brown adipose tissue.

FGF-1 and FGF-2 are widely expressed in adult tissues; see Baird et al. and Burgess et al, above. In contrast, most other FGFs and FHFs are narrowly expressed in adult tissues; see references cited above. Although the amino acid sequence of FGF-16 is highly homologous to that of FGF-9, the expression profile of FGF-16 is quite different from that of FGF-9, as well as from other members of the FGF family. Thus, FGF-16 appears to be a novel FGF which has a unique physiological role.

XII. Cloning of Human FGF-16

Using the information resulting from the cloning and sequencing of the gene for rat FGF-16, the gene for human FGF-16 was cloned and expressed as follows.

A partial cDNA sequence of rat FGF-16 (SEQ ID NO: 7), beginning at nucleotide 92 and ending at the nucleotide 637 of the nucleic acid sequence shown in FIG. 1, was utilized for the design of PCR primers for human FGF-16 DNA amplification. Some of the primer sequences were partially degenerate to increase the likelihood of primer annealing in spite of codon differences which might exist between rat and human FGF-16 DNA sequences. PCR products were cloned into either vector PCRII or vector PCR2.1 (Invitrogen, Carlsbad, Calif.) before sequencing. PCR amplification of rat genomic DNA verified that the position of the last intron in the FGF-16 coding region corresponds to the position of the intron in other members of the FGF family.

Human genomic DNA prepared from HeLa cells was amplified with combinations of the rat FGF-16 primers and the products were analyzed by polyacrylamide gel electrophoresis (PAGE). Products of PCR reactions whose size was unpredictable because the fragment being amplified spanned one or more introns were analyzed by nested PCR with primer pairs expected to lie within single exons. One such nested PCR, primed with a pair of oligonucleotides, specifically, 5'-CGG GAA CAG TTT GAA GAA AAC TGG TA-3' (SEQ ID NO: 8), corresponding to nucleotides 422–447 in the nucleic acid sequence in FIG. 1, and 5'-GAA AGT GNG TGA AYT TCT GRT G-3' (SEQ ID NO: 9), where "N" designates inosine, and which is complementary to nucleotides 554–575 of the nucleic acid sequence of FIGS. 1A–1B, yielded a PCR product of the expected size (0.15 kilobases), based on the full length rat FGF-16 sequence. In the nucleic acid sequence of SEQ ID NO: 9, "Y" represents a mixture of C and T and "R" represents a mixture of A and G, in accordance with IUB (International Union of Biochemistry) convention. Both the nested PCR product and the parent, intron-spanning PCR product [1.7 kilobases, primed with 5'-CCG CAC GGG CTT CCA CCT TGA-3' (SEQ ID NO: 10), which is homologous to nucleotides 217–237 of the rat nucleic acid sequence of FIGS. 1A–1B, and 5'-GAA AGT GIG TGA AYT TCT GRT G-3'] were cloned and sequenced. The sequence of the peptide predicted to be encoded by the exon sequences of this human FGF-16 genomic DNA fragment was highly homologous to rat FGF-16. First strand cDNA was synthesized from human heart polyA$^+$ RNA using a random primer adapter, 5'-GGC CGG ATA GGC CTC ACN NNN NNT-3' (SEQ ID NO: 11), with "N" representing a random mixture of the bases A,C,G and T. PCR (thirty five cycles) was performed with 5'-CGC GGC TCG CCC ACA GAC TTC-3' (SEQ ID NO: 12), corresponding to nucleotides 155–175 of the rat nucleic acid sequence of FIG. 1, and a unique sequence human FGF-16 PCR primer, 5'-CTG TCT CTC TGA GTC CGA ATG TT-3' (SEQ ID NO: 13), complementary to nucleotides 480–502 of the nucleic acid sequence of FIGS. 6A–6B, was designed based on the sequence of the human genomic fragment. The product band of approximately 340 base pairs in size was purified by PAGE and cloned into a pCRII vector (Invitrogen) for DNA sequencing. Human FGF-16 oligonucleotides were designed based on these sequences and used in 3'-RACE and 5'-RACE of human fetal brain cDNA and human heart cDNA to extend the cDNA sequence in both directions in order to obtain the complete coding sequence.

The 3'-RACE procedure was performed as follows. First-strand cDNA was prepared from human heart polyA$^+$ RNA (Clontech Laboratories, Inc., Palo Alto, Calif.) by standard methods using oligo-dT primer-adapter, 5'TTCGGCCGGATAGGCCTTTTTTTTTTTTT-3' (SEQ ID NO: 14), and Superscript (GIBCO-BRL) reverse transcriptase. The first-strand cDNA was used as template in 3'-RACE PCR (thirty cycles, annealing temperature 55° C.) primed with 100 nM each of 5'-TTCGGCCGGATAGGCCTTTTTTTTTTTTT-3' and 5'-CGG GAA CAG TTT GAA GAA AAC TGG TA-3'. In order to partially suppress priming by the oligo-dT primer-adapter without suppressing priming by the gene-specific FGF-16 primer, a nonpriming homolog, namely 5'TTCGGCCGGATAGGCCTTTTTTTTTTTTTp-3', where p represents a 3'-phosphate group, was added at a final concentration of 200 nM to this and subsequent 3'-RACE PCRs as a competitive inhibitor of annealing and priming by 5'TTCGGCCGGATAGGCCTTTTTTTTTTTTT-3'. Further amplification and enrichment of FGF-16 DNA was carried out by diluting 0.4 μl of the product of the first RACE PCR into 40 μl of fresh PCR mixture containing the same primers, and then continuing PCR for another eighteen cycles. A 0.4 μl aliquot of the product of this PCR was used as a template in a nested 3'-RACE PCR (twenty five cycles), priming with 5'-TTCGGCCGGATAGGCCTTTTTTTTTTTTT3', and a new human FGF-16 primer, namely 5'-GTA CAA CAC CTA TGC CTC AAC CT-3' (SEQ ID NO: 15), corresponding to nucleotides 451–473 of the human nucleic acid sequence of FIGS. 6A–6B, located downstream of 5'-CGG GAA CAG TTT GAA GAA AAC TGG TA-3'. The major band of the product of the nested PCR was cloned and sequenced. The sequence of this DNA fragment included the carboxy-terminal coding region and at least part of the 3'-UTR of the apparent human homolog of rat FGF-16.

Three successive cycles of 5'-RACE and DNA sequence determination were required to obtain the cDNA sequence encoding the amino-terminal portion of human FGF-16. 5'-RACE was performed on untailed first strand cDNA using a novel set of semi-random primer-adapters. Six partially random primers, each capable of priming within a large number of different cDNAs, but only at a small fraction of sites within any one cDNA such as FGF-16 cDNA, were utilized as upstream (5') primers in combination with FGF-16 gene-specific downstream (3') primers. Each partially random primer consisted of an eighteen-nucleotide unique adapter sequence, 5'GCAGTCGCTCCTTCCGTG-3' (SEQ ID NO: 16), followed by a nine-nucleotide random sequence, NNNNNNNNN (SEQ ID NO: 17), followed by a 4- or 5-nucleotide unique sequence such as 5'-CACA-3'.

First, human heart cDNA was used as template in thirty cycles of PCR with the mixture of five partially random sequence primers, namely 5'-GCAGTCGCTCCTTCCGTGNNNNNNNNNX-3' (SEQ ID NO: 18), where "N" designates random bases (A, C, T or G) and "X"=AATG, TCTC, TTGG, CACA or AACC, and an FGF-16 primer, 5'-CTC CTC GCT CAT TCA TTC CTA-3' (SEQ ID NO: 19), which was complementary to nucleotides 366–386 of the human nucleic acid sequence of FIG. 6. The first cycle of PCR was performed differently from the remaining cycles, to allow low stringency for annealing of the semi-random primers. In particular, the FGF-16 specific primer was not added until the second cycle, and the annealing step in the first cycle was performed at 25° C. in the presence of both Taq and Klenow DNA polymerases, followed by slow warming (ten minutes) to the Taq elongation temperature of 72° C. As the temperature was increased to 94° C. for initiation of the second cycle of PCR, the FGF-16 primer was added and PCR was continued. An aliquot of the product of this PCR was then used as template in a PCR (twenty cycles) with the adapter primer, 5'-GCAGTCGCTCCTTCCGTG-3', and 5'-AGT CCA CTC CCC GGA TGC TGA T-3' (SEQ ID NO: 20), the latter being complementary to nucleotides 332–353 of the human nucleic acid sequence of FIG. 6. The most prominent bands in the product of this PCR were cloned and sequenced, the sequence of one clone revealing the sequence of human FGF-16 beginning at nucleotide 149. The sequences of several clones contained an apparent intron and 3' splice site preceding nucleotide 298. The sequence of one clone revealed that the semi-random primer ending in the four base sequence CACA was annealing within the intron. To eliminate this unwanted priming event, this primer was omitted from the semi-random primer mix in the subsequent round of 5'-RACE. For this 5'-RACE, a mixture of the four remaining semi-random primers was incubated with human heart first-strand cDNA in a standard PCR mix with Taq polymerase and nucleoside triphosphates, but without a downstream FGF-16 primer, for periods of 10–15 minutes each at 25° C., 37° C., and 50° C., then one minute at 72° C. for strand elongation, before adding FGF-16 primer, 5'-AGT CCA CTC CCC GGA TGC TGA T-3', and adapter primer, 5'-GCAGTCGCTCCTTCCGTG-3', and proceeding with PCR for thirty cycles. An aliquot of the product was further amplified in a nesting PCR (eighteen cycles) with primers 5'-GCAGTCGCTCCTTCCGTG-3' and 5'-CTC CAG GAT TCC GAA GCG GCT GTG GTC GTG-3' (SEQ ID NO: 21), the latter being complementary to nucleotides 278–307 of the human nucleic acid sequence of FIG. 6, followed by a 10:1 dilution into an identical PCR mix lacking the competitor and another ten cycles of PCR. Although the resulting products appeared as a smear on gel electrophoresis, they were cloned into a pCRII vector and clones were obtained which contained the human FGF-16 sequence beginning at nucleotide 19.

A PCR technique similar to the 5'-RACE methods described above was used to amplify genomic DNA sequences including the amino-terminal coding sequence of human FGF-16. A semi-random adapter-primer, 5'-NNT ANN ACN CCA CNC AAN NNN NAT G-3' (SEQ ID NO: 22), with "N" at positions 1, 2, 5, 6, 9, 14 and 18 designating inosine, and "N" at positions 19, 20, 21 and 22 designating bases selected at random from among A, C, T and G, at a concentration of 2 $\mu$M, was used in a Klenow polymerase catalyzed DNA synthesis reaction at 25° C. with 100 ng of heat-denatured human genomic DNA as template. A 4-$\mu$l aliquot of the product was used as template in a PCR (thirty cycles; 40 $\mu$l) primed with adapter primer 5'-GGT AGG ACG CCA CGC AAG-3' (SEQ ID NO: 23) and FGF-16 3' primer, 5'-TCC GAA GCG GCT GTG GTC GTG-3' (SEQ ID NO: 24), the latter representing nucleotides 278–298 of the nucleic acid sequence of FIGS. 1A–1B, in the presence of an equimolar amount of competitive oligonucleotide 5'-GGT AGG ACG CCA CGC AAGp-3'. The product of this PCR was amplified further in a nested PCR (twenty cycles) with primers 5'-GGT AGG ACG CCA CGC AAG-3' and 5'-AAG ATC TCC AGG TGG AAG CCG-3', the latter being complementary to nucleotides 229–249 of the human nucleic acid sequence of FIGS. 6A–6B, again in the presence of an equimolar amount of the competitor, 5'-GGT AGG ACG CCA CGC AAGp-3'. The products were cloned into the vector PCR2.1 (Invitrogen). Colonies were screened for the presence of FGF-16 sequences by PCR with 5'-GGA TCT ACA CGG CTT CTC CTC GTC T-3' (SEQ ID NO: 25), representing nucleotides 61–85 of the nucleic acid sequence of FIGS. 6A–6B, and 5'-CTG GGG AGT CAG CTA AGG GCA-3' (SEQ ID NO: 26), representing nucleotides 96–116 of the nucleic acid sequence of FIGS. 1A–1B, and by colony hybridizations with $^{32}$P-labelled oligonucleotide 5'-GGA TCT ACA CGG CTT CTC CTC GTC T-3'. The sequences of these clones contained the sequence of the amino terminus of human FGF-16, completing the sequence of the human FGF-16 coding region (FIGS. 6A–6B, SEQ ID NO: 5).

XIII. Recombinant Expression of Rat FGF-16

To provide sufficient quantities of material for biological characterization, rat FGF-16 polypeptides were expressed recombinantly in bacterial cells as follows.

A) Construction of Expression Vectors. Vectors for recombinant expression in bacterial cells were constructed in the following manner.

1) Preparation of pAMG21rFGF-16. The full length cDNA for rat FGF-16 described above (FIGS. 1A–1B, SEQ ID NO. 1) was cloned into pGEM-T plasmid vector (Promega, Madison, Wis.). Using standard molecular biology techniques and protocols suggested by the manufacturer, the rat FGF-16 (rFGF-16) insert was cloned into plasmid vector pAMG21 (American Type Culture Collection, Rockville, Md., Accession No. 98113).

Oligonucleotide amplimers for PCR were designed to be partly homologous to the rFGF-16 sequence at the 5' and 3' terminal ends of the rFGF-16 insert in pGEM-T rFGF-16 and to contain the restriction endonuclease recognition sites NdeI and KpnI, respectively. PCR was performed using the following primers: AAA CAA CAT ATG GCT GAA GTTGGT GGT GTC TTT GCC TCC TTG GA (SEQ ID NO: 27) and AAA CAA GGT ACC TTT ACC TAT AGC GGA AGA GGT (SEQ ID NO: 28) (with regions homologous to rFGF-16 underlined) and pGEM-T rFGF-16 (AmpliTaq DNA Polymerase, Perkin-Elmer, Foster City, Calif.) as the template. This PCR product was purified (QIAquick™ PCR purification Kit, QIAGEN, Santa Clarita, Calif.) and then digested with restriction endonucleases NdeI and KpnI (Boehringer Mannheim, Indianapolis, Ind.). The resulting 631-base pair DNA fragment was purified by agarose gel extraction (QIAquick™ Gel Extraction Kit, QIAGEN) and ligated with similarly purified 6.067-kilobase pAMG21 vector fragment (ATCC #98113). Transformation of the appropriate E. coli host strain (GM120, ATCC #55764) with this ligation reaction (Gene Pulser®, BioRad, Richmond, Calif.) was plated on Luria agar plates with 40 µg/ml of kanamycin to select for recombinant bacteria. No colonies were obtained. Selection in liquid culture with kanamycin and subsequent plating on Luria agar plates with 40 µg/ml of kanamycin failed to recover any viable colonies. However, PCR of the ligation reaction using a primer at the 3' end of the rFGF-16 insert and a vector primer 5' to the rFGF-16 insert, CGT ACA GGT TTA CGC AAG AAA ATG G (SEQ ID NO: 29), revealed that the correct plasmid construct was present in the ligation. This PCR product was purified (QIAquick™ PCR Purification Kit) and then cut with restriction endonucleases XbaI and KpnI (Boehringer Mannheim). The resultant 667-base pair DNA fragment was purified by agarose gel extraction (QIAquick™ Gel Extraction Kit) and ligated with the similarly purified pAMG21 6.031-kilobase KpnI-PstI DNA fragment. Transformation of the appropriate E. coli host strain (GM120; ATCC #55764) with this ligation (Gene Pulsere®, BioRad) yielded kanamycin-resistant colonies. Plasmid DNA was purified from one of these colonies (QIAGEN® Plasmid Kit, QIAGEN) and the DNA sequence was confirmed.

2) Preparation of pAMG21ΔN34rFGF-16. Using standard molecular biology techniques and protocols suggested by the manufacturer, pAMG21ΔN34rFGF-16 was cloned by ligation of NdeI-PstI oligonucleotide linkers TAT GAA CGA GCG CCT GGG CCA GAT CGA GGG GAA GCT GCA (SEQ ID NO: 30) and GCT TCC CCT CGA TCT GGC CCA GGC GCT CGT TCA (SEQ ID NO: 31) with a 6.56-kilobase PstI-NdeI DNA fragment of pAMG21rFGF-16, above, purified by agarose gel extraction (QIAquick™ Gel Extraction Kit, QIAGEN). The linkers were kinased and annealed (Polynucleotide Kinase, Boehringer Mannheim) prior to ligation (T4 DNA ligase, Boehringer Mannheim). The pAMG21 vector plasmid (ATCC #98113) contains a kanamycin resistance gene, thus transformation of the appropriate E. coli host strain (GM120; ATCC #55764) with this ligation reaction (Gene Pulser®, BioRad) yielded kanamycin-resistant colonies on Luria agar plates using 40 µ/ml of kanamycin in the growth medium. Plasmid DNA was purified from one of these colonies (QIAGEN® Plasmid Kit, QIAGEN) and the DNA sequence was confirmed.

B) Expression of Full Length Rat FGF-16 in E. Coli.

Full-length rat FGF-16(FIGS. 1A–1B, SEQ ID NO: 1) was expressed in E. coli using pAMG21rFGF-16. The cells were grown in a ten-liter fermentor at pH 7 and a temperature of 30° C. Dissolved oxygen levels were maintained greater than or equal to fifty percent. When the fermentation medium reached an optical density of 10, the cells were induced using ten milliliters of stock solution composed of 500 nanograms per milliter (ng/ml) of N-(beta-ketocaproyl)-dl-homoserine lactone (Sigma Chemical Company, St. Louis, Miss.). After a twelve-hour induction period, the fermentation medium was chilled and the cells were mechanically lysed in water and centrifuged at 10,000 revolutions per minute (rpm) for two hours. The supernatant was subjected to SP-Sepharose ion-exchange column chromatography in 50 mM Tris HCl, pH 7.5. The bound proteins were eluted with a linear NaCl gradient. Fractions eluting around 0.3–0.6M NaCl contained many bands, ranging in molecular weight between 15,000 and 28,000. Sequence analysis of these protein bands after electroblotting showed both intact and N-terminally truncated forms. One of the bands had an N-terminal sequence of NRE (i.e., asparagine-arginine-glutamic acid) and appeared to be the smallest in size before undergoing extensive proteolytic digestions. In addition to full length rat FGF-16 (SEQ ID NO: 1), the resulting cell paste included a truncation product in which cleavage had occurred between leucine 34 and asparagine 35 ("des-N-34") (SEQ ID NO: 32), as well as a truncation product in which cleavage had occurred between alanine 9 and serine 10 ("des-N-9") (SEQ ID NO: 33).

FGF-16 has sequence homology to FGF-9, with seventy three percent of the amino acid residues being identical between the full length polypeptides of mature human FGF-9 and FGF-16. Both of these FGFs lack signal sequence, as is the case for acidic FGF and basic FGF. Nevertheless, human FGF-9 has been observed to be efficiently secreted into the conditioned medium of COS cells transfected with hFGF-9 cDNA. Sequence analysis of purified samples showed an intact N-terminus and a truncation between leucine 33 and serine 34. This des-N-33 form of FGF-9 has been found to be as active as the full-length FGF-9 form in a preliminary in vitro bioassay. When FGF-9 and FGF-16 are aligned based on sequence identity, the N-terminal cleavage sites observed for FGF-9 and FGF-16 are located nearly at the same position. Consequently, it was decided to evaluate the des-N-34 form of rat FGF-16, instead of full length, for biological activity.

C) Expression of Des-N-34 Rat FGF-16 in E. Coli. E. coli cells transformed with pAMG21ΔN34rFGF-16, containing cDNA encoding the des-N-34 form of rat FGF-16, were grown under the above mentioned conditions and mechanically lysed in 1M ammonium sulfate, 50 mM Tris HCl, pH 7.5 at 100 g/l. The lysed suspension was centrifuged at 4° C. and 10,000 rpm for two hours. The supernatant was batch-bound to phenyl-Sepharose in 1M ammonium sulfate, 50 mM Tris HCl, pH 7.5. The resin was extensively washed with the same buffer in a glass filter and transferred to a column. The bound proteins were further washed with the same buffer in the column and then eluted with a linear descending ammonium sulfate gradient from 1to 0M. The fractions were analyzed by SDS-PAGE, and those fractions containing des-N-34 rat FGF-16 were pooled.

The resulting pool was mixed with 3.5 volumes of cold water and batch-bound to SP-Sepharose equilibrated in 50 mM Tris HCl, pH 7.0. The SP-Sepharose was packed into a column and the bound proteins were eluted with a linear NaCl gradient from 0to 1M. Based on SDS-PAGE of the eluted material, the fractions containing the des-N-34 form of rat FGF-16 were pooled, then dialyzed against 1M ammonium sulfate, 50 mM Tris HCl, pH 7.0. The dialyzed material was loaded onto phenyl-Sepharose equilibrated in 1M ammonium sulfate, 50 mM Tris HCl, pH 7.0. After extensive washing with the same buffer, the bound proteins were eluted with a linear ammonium sulfate gradient from 1 to 0M. The fractions containing des-N-34 rat FGF-16 in amounts greater than ninety percent were pooled and dialyzed against PBS buffer as a final product. Inclusion of 0.1–10 mM EDTA during purification increased the recovery of the final product. This procedure, including the use of 0.1 mM EDTA, also resulted in the efficient purification of the full length form of rat FGF-16 when applied to lysates of E. coli cells that had been transformed with the full length cDNA for rat FGF-16.

XIV. In Vivo Biological Testing of E. Coli-Derived Rat FGF-16

The in vivo biological effects of the des-N-34 form of E. coli-derived recombinant rat FGF-16 were evaluated in normal mice as follows.

A. In Vivo Administration to Mice. Five female BDF1 mice were administered recombinant des-N-34 rat FGF-16 (SEQ ID NO: 32) via intraperitoneal injection (IP) at a dose of 5 mg/kg/day for seven days. Separately, a group of five female BDF1 mice received a control buffer solution under the same conditions. All of the mice were injected with 50 mg/kg of bromodeoxyuridine (BrdU) (Aldrich Chemical Company, Milwaukee, Wis.) one hour prior to harvest, radiographed, and then sacrificed. Body and selected organ weights were measured, blood was drawn for hematology and serum chemistries, and organs were harvested for histologic analysis and BrdU labeling.

Blood samples were analyzed for clinical chemistries on a Hitachi 717 System (Boehringer Mannheim) or complete blood count on a Technicon H1E Analyzer (Miles Technicon Instrument Corp., Tarrytown, N.Y.). BrdU immunohistochemical staining was done on 4-millimeter thick paraffin embedded sections using an automated TechMate Immunostainer (BioTek Solutions, Santa Barbara, Calif.). Sections were first digested with 0.1% protease (Sigma Chemical, St. Louis, Mo.), followed by 2N HCl. BrdU was detected with a rat monoclonal antibody (MAb) to BrdU (Accurate Chemical, Westbury, N.Y.) followed by a biotinylated anti-rabbit/anti-mouse secondary cocktail (BioTek) and an ABC tertiary coupled to alkaline phosphatase (BioTek). The staining reaction was visualized with BioTek Red chromagen.

BrdU-labeled hepatocytes were quantified by a pathologist blinded to the treatment groups by counting BrdU-labeled hepatocytes in ten random microscopic high powered fields (HPF—40× objective) per liver section and determining the mean number of BrdU-positive hepatocytes per HPF.

B. Gross Pathology Results. The livers and spleens from mice injected with des-N-34 rat FGF-16 were significantly larger than those of buffer control injected mice. These results are summarized in Table 1, below.

C. Clinical Pathology Results. Mice injected with des-N-34 rat FGF-16 had significant increases in serum triglycerides, lactate dehydrogenase (LDH) and total protein, and a significant decrease in serum alkaline phosphatase. These results are also summarized in Table 1.

D. Histopathology Results. Hematoxylin and eosin (H&E) and BrdU-stained sections of liver, spleen, lung, brain, heart, kidney, adrenal, stomach, small intestine, pancreas, cecum, colon, mesenteric lymph node, skin, mammary gland, trachea, esophagus, thyroid, parathyroid, salivary gland, urinary bladder, ovary, bone and bone marrow were examined from the five des-34 FGF-16 injected mice and five buffer control-injected mice. The only significant histologic finding was a significant increase in BrdU-positive hepatocytes per microscopic high powered field in (des-34)FGF-16 treated mice compared to buffer control-injected mice (see Table 1 and FIG. 7).

TABLE 1

SELECTED ORGAN WEIGHTS, SERUM CHEMISTRIES AND HEPATOCELLULAR BRDU LABELING IN FGF-16 TREATED MICE

|  | FGF-16 Treated Mice (n = 5) | Buffer Control Injected Mice (n = 5) | p value |
| --- | --- | --- | --- |
| Liver Weight as Percent of Body Weight | 6.06 ± 0.36 SD | 5.09 ± 0.14 SD | 0.0005 |
| Spleen Weight as Percent of Body Weight | 0.35 ± 0.04 SD | 0.29 ± 0.03 SD | 0.02 |
| Triglycerides (mg/dl) | 193 ± 43 SD | 125 ± 45 SD | 0.04 |
| Lactate Dehydrogenase (IU/1) | 250 ± 29 SD | 193 ± 32 SD | 0.02 |
| Total Serum Protein (mg/dl) | 5.5 ± 0.4 SD | 4.9 ± 0.2 SD | 0.02 |
| Alkaline Phosphatase (IU/1) | 56 ± 8 SD | 166 ± 27 SD | less than 0.0001 |
| BrdU-Positive Hepatocytes per High Powered Field | 7.28 ± 4.08 SD | 0.27 ± 0.52 SD (n = 3) | 0.002 |

E. Conclusions. Mice injected with des-N-34 rat FGF-16 exhibited an increase in hepatocellular BrdU labeling and a moderate, but significant, increase in liver weight, serum triglycerides, serum LDH and total serum protein, together with a decrease in serum alkaline phosphatase. Thus, FGF-16 induces hepatocellular proliferation and increased hepatic production of triglycerides and serum proteins, such as albumin. These in vivo effects are similar to, but of slightly lesser magnitude than, the hepatic effects induced by FGF-7 (KGF); see Housley et al., Journal of Clinical Investigation, Volume 94, pages 1764–1777 (1994). The present findings indicate the potential effectiveness of FGF-16 in applications in which an increase in hepatocellular stimulation, proliferation and/or differentiation is required. Such applications include increasing liver function to treat or prevent hepatic cirrhosis, fulminant liver failure, damage caused by acute viral hepatitis and/or toxic insults to the liver.

Particular methods of therapy for this purpose may include the transfection of endogenous hepatocyte cells in the host organism or subject being treated with a vector comprising regulatory elements, such as those which have been described, operatively linked to a DNA molecule encoding FGF-16 or an analog thereof in order to effect expression in situ.

The invention described above is now defined in the appended claims.

What is claimed is:

1. An isolated nucleic acid molecule encoding a polypeptide having an amino acid sequence selected from the group consisting of SEQ ID NO: 2, SEQ ID NO: 5, and truncations thereof in which from one to thirty-four amino acids have been deleted from the N-terminus or from one to eighteen amino acids have been deleted from the C-terminus, said full length or truncated polypeptide having hepatocyte proliferation and growth activity.

2. A nucleic acid molecule according to claim 1 which encodes the polypeptide of SEQ ID NO: 2 and has the nucleotide sequence of SEQ ID NO: 1.

3. A nucleic acid molecule according to claim 1 which encodes the polypeptide of SEQ ID NO: 5 and has the nucleotide sequence of SEQ ID NO: 4.

4. An expression vector comprising expression regulatory elements operatively linked to a nucleic acid molecule according to claim 1.

5. An expression vector according to claim 4 in which the nucleic acid molecule has the nucleotide sequence of SEQ ID NO: 1.

6. An expression vector according to claim 4 in which the nucleic acid molecule has the nucleotide sequence of SEQ ID NO: 4.

7. A host cell transformed or transfected with a nucleic acid molecule according to claim 1.

8. A host cell transformed or transfected with an expression vector according to claim 4.

9. A transformed or transfected host cell according to claims 7 or 8 which is prokaryotic or eukaryotic.

10. A transformed or transfected host cell according to claim 9 which is an animal cell.

11. A transformed or transfected host cell according to claim 9 which is a bacterial cell.

12. A transformed or transfected host cell according to claim 11 which is an *E. coli* cell.

13. A method for expressing a polypeptide having an amino acid sequence selected from the group consisting of: SEQ ID NO: 2, SEQ ID NO: 5 and truncations thereof in which from one to thirty-four amino acids have been deleted from the N-terminus or from one to eighteen amino acids have been deleted from the C-terminus, wherein said full length polypeptide or fragment has hepatocyte proliferation and growth activity, comprising:

culturing host cells containing a DNA molecule encoding said full length or truncated polypeptide operatively linked to regulatory elements for stimulating the expression thereof, under conditions such that the DNA molecule is expressed, and isolating the expressed full length or truncated polypeptide from the host cell culture.

14. A method according to claim 13 in which the DNA molecule is a cDNA.

15. A method according to claim 13 in which the host cells are *E. coli* cells.

16. A method according to claim 13 in which the host cells are animal cells.

17. A nucleic acid molecule according to claim 1 which encodes a truncated polypeptide having the amino acid sequence of SEQ ID NO: 32.

18. A nucleic acid molecule according to claim 1 which encodes a truncated polypeptide having the amino acid sequence of SEQ ID NO: 33.

19. A method according to claim 13 in which the truncated polypeptide has an amino acid sequence selected from the group consisting of SEQ ID NO: 32 and SEQ ID NO: 33.

* * * * *

UNITED STATES PATENT AND TRADEMARK OFFICE
CERTIFICATE OF CORRECTION

PATENT NO. : 5,998,170

DATED : December 7, 1999

INVENTOR(S) : Arakawa et al.

It is certified that error appears in the above-identified patent and that said Letters Patent is hereby corrected as shown below:

Column 1, line 17: Change "FGF-1to" to -- FGF-1 to --

Column 1, line 54: Change "poylmerase" to -- polymerase --.

Column 7, line 63: Change "to set above" to -- to above --.

Column 8, line 8: Change "Met$^{31\ 1}$" to -- Met$^1$ --.

Column 11, line 39: Change "tendnency" to -- tendency --.

Column 13, line 1: Change "Aoplications" to -- Applications --

Column 16, line 22: Change "memebers" to -- members --.

Column 19, line 53: Change "nucleoside" to -- nucleotide --.

Column 20, lines 56 and 57: Change " Rockville, Md. " to -- 10801 University Blvd., Manassas, VA 20110-2209 --.

Column 21, line 50: Change "μ/ml" to -- μg/ml --.

Signed and Sealed this

Twenty-seventh Day of March, 2001

Attest:

NICHOLAS P. GODICI

Attesting Officer

Acting Director of the United States Patent and Trademark Office